US012371730B2

(12) United States Patent
Okada et al.

(10) Patent No.: US 12,371,730 B2
(45) Date of Patent: Jul. 29, 2025

(54) FLUOROGENIC NUCLEIC ACID MOLECULE AND TARGET RNA FLUORESCENT LABELING METHOD

(71) Applicant: JAPAN SCIENCE AND TECHNOLOGY AGENCY, Saitama (JP)

(72) Inventors: Yasushi Okada, Osaka (JP); Tetsuro Ariyoshi, Tokyo (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 1072 days.

(21) Appl. No.: 17/299,018

(22) PCT Filed: Dec. 3, 2019

(86) PCT No.: PCT/JP2019/047228

§ 371 (c)(1),
(2) Date: Jun. 2, 2021

(87) PCT Pub. No.: WO2020/116446

PCT Pub. Date: Jun. 11, 2020

(65) Prior Publication Data

US 2022/0177948 A1 Jun. 9, 2022

(30) Foreign Application Priority Data

Dec. 3, 2018 (JP) ................................ 2018-226743

(51) Int. Cl.
*C12Q 1/6806* (2018.01)
*C12Q 1/6825* (2018.01)
*C12Q 1/6876* (2018.01)

(52) U.S. Cl.
CPC ......... *C12Q 1/6806* (2013.01); *C12Q 1/6825* (2013.01); *C12Q 1/6876* (2013.01)

(58) Field of Classification Search
CPC .................................................... C12Q 1/6876
See application file for complete search history.

(56) References Cited

U.S. PATENT DOCUMENTS

| | | | |
|---|---|---|---|
| 9,664,676 | B2 | 5/2017 | Jaffrey et al. |
| 2015/0141282 | A1 | 5/2015 | Jaffrey et al. |

FOREIGN PATENT DOCUMENTS

| | | | |
|---|---|---|---|
| EP | 3211083 A1 | 8/2017 | |
| JP | 2001025400 A | 1/2001 | |
| WO | 2013016694 A2 | 1/2013 | |

OTHER PUBLICATIONS

Einert, Thomas R., and Roland R. Netz. "Theory for RNA folding, stretching, and melting including loops and salt." Biophysical journal 100.11 (2011): 2745-2753. (Year: 2011).*
Zuker, Michael. "Mfold ©: RNA modeling program." GERF Bulletin of Biosciences 1 (2010): 1-6. (Year: 2010).*
Office Action issued by the State Intellectual Property Office of the Peoples Republic of China for Application No. 201980079072.0, Mar. 26, 2024, China.
Japan Patent Office, "International Search Report for PCT Application No. PCT/JP2019/047228", Japan, Mar. 3, 2020.
Bin Wu et al., "Translation dynamics of single mRNAs in live cells and neurons", Science, 2016, vol. 352, pp. 1430-1435.
Sanjay Tyagi, "Imaging intracellular RNA distribution and dynamics in living cells", Nature Methods, 2009, vol. 6, pp. 331-338.
Jeremy S. Paige et al., "RNA Mimics of Green Fluorescent Protein", Science, 2011, vol. 333, pp. 642-646.
Grigory S. Filonov et al., "Broccoli: Rapid Selection of an RNA Mimic of Green Fluorescent Protein by Fluorescence-Based Selection and Directed Evolution", Journal of the American Chemical Society, 2014, vol. 136, pp. 16299-16308.
Grigory S. Filonov et al., "RNA Imaging with Dimeric Broccoli in Live Bacterial and Mammalian Cells", Current Protocols in Chemical Biology, 2017, vol. 8(1), pp. 1-28.
Simon Ketterer et al., "Systematic reconstruction of binding and stability landscapes of the fluorogenic aptamer spinach", Nucleic Acids Research, 2015, vol. 43, pp. 9564-9572.
Alexis Autour et al., "iSpinach: a fluorogenic RNA aptamer optimized for in vitro applications", Nucleic Acids Research, 2016, vol. 44, pp. 2491-2500.
Jiawei Zou et al., "Selection of Intracellularly Functional RNA Mimics of Green Fluorescent Protein Using Fluorescence-Activated Cell Sorting", Journal of Molecular Evolution, 2015, vol. 81, pp. 172-178.
Eman A. Ageely et al., "Quadruplex-Flanking Stem Structures Modulate the Stability and Metal Ion Preferences of RNA Mimics of GFP", ACS Chemical Biology, 2016, vol. 11, pp. 2398-2406.
Grigory S. Filonov et al., "In-Gel Imaging of RNA Processing Using Broccoli Reveals Optimal Aptamer Expression Strategies", Chemistry & Biology, 2015, vol. 22, pp. 649-660.

(Continued)

*Primary Examiner* — Robert J Yamasaki
(74) *Attorney, Agent, or Firm* — Troutman Pepper Locke LLP; Tim Tingkang Xia, Esq.

(57) ABSTRACT

The present invention provides a fluorogenic RNA capable of visualizing mRNA in cells, particularly, living mammalian cells, and a target RNA fluorescent labeling method using the fluorogenic RNA. The present invention provides a fluorogenic nucleic acid molecule containing a base sequence having two or more fluorescent molecule-binding regions linked via a linker sequence, in which one or more fluorescent molecule-binding aptamer sequences are inserted into a scaffold sequence of each of the fluorescent molecule-binding regions.

14 Claims, 8 Drawing Sheets

Specification includes a Sequence Listing.

(56) References Cited

OTHER PUBLICATIONS

Grigory S. Filonov et al., "Bright and stable near-infrared fluorescent protein for in vivo imaging", Nature Biotechnology, 2011, vol. 29, pp. 757-761.
Akira Takai et al., Expanded palette of Nano-lanterns for real-time multicolor luminescence imaging, Proceedings of the National Academy of Sciences of the United States of America, 2015, vol. 112, pp. 4352-4356.
Michael Zuker, "Mfold web server for nucleic acid folding and hybridization prediction:, Nucleic Acids Research", 2003, vol. 31, No. 13, pp. 3406-3415.
Kenta Teralet al., "Two Decades of Genetically Encoded Biosensors Based on Forster Resonance Energy Transfer", Cell Structure and Function, 2019, vol. 44, pp. 153-169.
W. Russ Algar et al., "FRET as a biomolecular research tool—understanding its potential while avoiding pitfalls", Nature Methods, 2019, vol. 16, pp. 815-829.
Mette D.E. Jepson et al., "Development of a genetically encodable FRET system using fluorescent RNA aptamers", Nature Communications, 2018, vol. 9, Article No. 18.
Kyu Young Han et al., "Understanding the Photophysics of the Spinach-DFHBI RNA Aptamer-Fluorogen Complex to Improve Live-Cell RNA Imaging", Journal of the American Chemical Society, 2013, vol. 135, pp. 19033-19038.
Robert J. Trachman et al., "Structural Principles of Fluorescent RNA Aptamers", Trends in Pharmacological Sciences, 2017, vol. 38(10), p. 928-939.
Junjie U. Guo et al., "RNA G-quadruplexes are globally unfolded in eukaryotic cells and depleted in bacteria", Science, 2016, vol. 353(6306), p. 1382.
Ariyoshi T. et al, "Visualization of transcriptional dynamics at single-cell resolution with a genetically-encoded fluorogenic RNA.", Molecular Biology of the Cell, 2017, vol. 28, No. 26, p. 3727.
Ariyoshi T. et al, "Measurement of transcriptional dynamics in single living cells with a genetically-encoded fluorescent RNA.", Journal of Pharmacological Sciences, 2017, vol. 133, No. 3, p. S261(3-P-103).
Ariyoshi T. et al., "Visualization of transcriptional dynamics in single living cells using novel RNA aptamers", Programs and abstracts of the annual meeting of the molecular biology society of Japan, 2016, vol. 39, 1AS7-4.
Ariyoshi T. et al., "Visualizing spatiotemporal mRNA dynamics at subcellular resolution with a bright fluorogenic RNA.", Molecular Biology of the Cell, 2018, vol. 29, No. 26, p. 3063.
Office Action issued by the Japan Patent Office for Application No. 2020-559225, Apr. 5, 2022, Japan.
Grigory S. Filonov et al., In-Gel Imaging of RNA Processing Using Broccoli Reveals Optimal Aptamer Expression Strategies, Chemistry & Biology, 2015, vol. 22, pp. 649-660 (suppl. info. pp. 1-29).
Eman A. Ageely et al., Quadruplex-Flanking Stem Structures Modulate the Stability and Metal Ion Preferences of RNA Mimics of GFP, ACS Chemical Biology, 2016, vol. 11, pp. 2398-2406 suppor. info. pp. 1-4.
Extended Search Report issued by the European Patent Office for Application No. 19892242.9, Aug. 3, 2022, Europe.
Elena V. Dolgosheina et al: "Fluorophore-binding RNA aptamers and their applications : Fluorophore-binding RNA aptamers", Wiley Interdisciplinary Reviews: RNA, vol. 7, No. 6, Nov. 1, 2016 (Nov. 1, 2016), pp. 843-851, XP55487089, United Kingdom, ISSN: 1757-7004, DOI: 10.1002/wrna.1383.
Elena V. Dolgosheina et al: "RNA Mango Aptamer-Fluorophore: A Bright, High-Affinity Complex for RNA Labeling and Tracking", ACS Chemical Biology, vol. 9, No. 10, Aug. 21, 2014 (Aug. 21, 2014), pp. 2412-2420, XP55486675, ISSN: 1554-8929, DOI: 10.1021/cb500499x.

* cited by examiner

| | #1 | #2 | #3 | #4 | #5 | #6 | #7 | #8 | #9 | #10 | #11 | #12 | #13 | #14 | #15 | #16 | #17 |
|---|---|---|---|---|---|---|---|---|---|---|---|---|---|---|---|---|---|
| Fluorophore-binding sequence | Bro | Bro | Bro | Bro | Bro | Bro | dBro | dBro | dBro | Bro3 | Bro3 | Bro3 | Bro3 | Bro3 | Bro3 | Bro3 | Bro3 |
| Number of fluorophore-binding sites | 1 | 2 | 4 | 8 | 12 | 12 | 4 | 8 | 12 | 1 | 2 | 4 | 8 | 12 | 12 | 12 | 12 |
| Scaffold | None | F30 | F30 | F30 | F30 | None | F30 | F30 | F30 | None | F30 | F30 | F30 | F30 | F30 | None | None |
| Stem-loop length (bp) | 5 | 5 | 5 | 5 | 5 | 5 | 5 | 5 | 5 | 5 | 5 | 5 | 5 | 5 | 6 | 5 | 6 |

SEQUENCE LISTING

```
<160> NUMBER OF SEQ ID NOS: 46

<210> SEQ ID NO 1
<211> LENGTH: 15
<212> TYPE: RNA
<213> ORGANISM: Artificial Sequence
<220> FEATURE:
```

-continued

<223> OTHER INFORMATION: The sequence at the 5' end of the stem/loop of the consensus sequence

<400> SEQUENCE: 1
gwgavgghcg ggucc 15

<210> SEQ ID NO 2
<211> LENGTH: 20
<212> TYPE: RNA
<213> ORGANISM: Artificial Sequence
<220> FEATURE:
<223> OTHER INFORMATION: The sequence at the 3' end of the stem/loop of the consensus sequence

<400> SEQUENCE: 2
guygaguaga gugugrgcuc 20

<210> SEQ ID NO 3
<211> LENGTH: 14
<212> TYPE: RNA
<213> ORGANISM: Artificial Sequence
<220> FEATURE:
<223> OTHER INFORMATION: The sequence of the stem/loop structure region

<400> SEQUENCE: 3
agauauuaau aucu 14

<210> SEQ ID NO 4
<211> LENGTH: 14
<212> TYPE: RNA
<213> ORGANISM: Artificial Sequence
<220> FEATURE:
<223> OTHER INFORMATION: The sequence of the stem/loop structure region

<400> SEQUENCE: 4
agauauucgu aucu 14

<210> SEQ ID NO 5
<211> LENGTH: 14
<212> TYPE: RNA
<213> ORGANISM: Artificial Sequence
<220> FEATURE:
<223> OTHER INFORMATION: The sequence of the stem/loop structure region

<400> SEQUENCE: 5
aguaguucgc uacu 14

<210> SEQ ID NO 6
<211> LENGTH: 16
<212> TYPE: RNA
<213> ORGANISM: Artificial Sequence
<220> FEATURE:
<223> OTHER INFORMATION: The sequence of the stem/loop structure region

<400> SEQUENCE: 6
aguagcuucg gcuacu 16

<210> SEQ ID NO 7
<211> LENGTH: 16
<212> TYPE: RNA
<213> ORGANISM: Artificial Sequence
<220> FEATURE:
<223> OTHER INFORMATION: The sequence of the stem/loop structure region

<400> SEQUENCE: 7
agcugcuucg gcagcu 16

<210> SEQ ID NO 8
<211> LENGTH: 49
<212> TYPE: RNA
<213> ORGANISM: Artificial Sequence
<220> FEATURE:
<223> OTHER INFORMATION: Baby Spinach

<400> SEQUENCE: 8
gugaaggacg gguccaguag uucgcuacug uugaguagag ugugagcuc 49

<210> SEQ ID NO 9
<211> LENGTH: 51
<212> TYPE: RNA
<213> ORGANISM: Artificial Sequence
<220> FEATURE:
<223> OTHER INFORMATION: Optimized Spinach

<400> SEQUENCE: 9
gagaaggacg gguccagcug cuucggcagc uguugaguag agugugagcu c 51

<210> SEQ ID NO 10
<211> LENGTH: 51
<212> TYPE: RNA
<213> ORGANISM: Artificial Sequence
<220> FEATURE:
<223> OTHER INFORMATION: iSpinach

<400> SEQUENCE: 10
gugagggucg gguccaguag cuucggcuac uguugaguag agugugggcu c 51

<210> SEQ ID NO 11
<211> LENGTH: 47
<212> TYPE: RNA
<213> ORGANISM: Artificial Sequence
<220> FEATURE:
<223> OTHER INFORMATION: ZT-324

<400> SEQUENCE: 11
gugaaggccg gguccagccg ugaggcuguu gaguagagug ugagcuc 47

<210> SEQ ID NO 12
<211> LENGTH: 49
<212> TYPE: RNA
<213> ORGANISM: Artificial Sequence
<220> FEATURE:
<223> OTHER INFORMATION: Broccoli

<400> SEQUENCE: 12
gagacggucg gguccagaua uucguaucug ucgaguagag ugugggcuc 49

<210> SEQ ID NO 13
<211> LENGTH: 49
<212> TYPE: RNA
<213> ORGANISM: Artificial Sequence
<220> FEATURE:
<223> OTHER INFORMATION: Broccoli3

<400> SEQUENCE: 13
gagacggucg gguccagaua uuaauaucug uugaguagag ugugggcuc 49

<210> SEQ ID NO 14
<211> LENGTH: 92
<212> TYPE: RNA
<213> ORGANISM: Artificial Sequence
<220> FEATURE:

<223> OTHER INFORMATION: dBroccoli

<400> SEQUENCE: 14
gagacggucg gguccaucug agacggucgg guccagauau ucguaucugu cgaguagagu 60
gugggcucag augucgagua gagugugggc uc 92

<210> SEQ ID NO 15
<211> LENGTH: 57
<212> TYPE: RNA
<213> ORGANISM: Artificial Sequence
<220> FEATURE:
<223> OTHER INFORMATION: F30 scaffold

<400> SEQUENCE: 15
uugccaugug uaugugggcc acauacucug augaucccuuc gggaucauuc auggcaa 57

<210> SEQ ID NO 16
<211> LENGTH: 105
<212> TYPE: RNA
<213> ORGANISM: Artificial Sequence
<220> FEATURE:
<223> OTHER INFORMATION: F30-Broccoli3

<400> SEQUENCE: 16
uugccaugug uaugugggag acggucgggu ccagauauua auaucuguug aguagagugu 60
gggcucccac auacucugau gauccuucgg gaucauucau ggcaa 105

<210> SEQ ID NO 17
<211> LENGTH: 150
<212> TYPE: RNA
<213> ORGANISM: Artificial Sequence
<220> FEATURE:
<223> OTHER INFORMATION: F30-2xBroccoli3

<400> SEQUENCE: 17
uugccaugug uaugugggag acggucgggu ccagauauua auaucuguug aguagagugu 60
gggcucccac auacucugau gauccgagac ggucgggucc agauauuaau aucuguugag 120
uagagugugg gcucggauca uucauggcaa 150

<210> SEQ ID NO 18
<211> LENGTH: 30
<212> TYPE: RNA
<213> ORGANISM: Artificial Sequence
<220> FEATURE:
<223> OTHER INFORMATION: Linker (30nt)

<400> SEQUENCE: 18
caguggggca gcggccgguc gucuggggga 30

<210> SEQ ID NO 19
<211> LENGTH: 44
<212> TYPE: RNA
<213> ORGANISM: Artificial Sequence
<220> FEATURE:
<223> OTHER INFORMATION: Linker (44nt)

<400> SEQUENCE: 19
cagacguugu ccgccuugug cggccgaucg acugaggaua ugaa 44

<210> SEQ ID NO 20
<211> LENGTH: 66
<212> TYPE: RNA
<213> ORGANISM: Artificial Sequence -continued
<220> FEATURE:
<223> OTHER INFORMATION: Linker (66nt)

<400> SEQUENCE: 20
ggaucauuca uggcaaucua gcaccuucgc ggccgaacau acaacugcuu gccaugugua 60
uguggg 66

<210> SEQ ID NO 21
<211> LENGTH: 33
<212> TYPE: PRT
<213> ORGANISM: Artificial Sequence
<220> FEATURE:
<223> OTHER INFORMATION: 3xNLS

<400> SEQUENCE: 21

Leu Val Pro Lys Lys Lys Arg Lys Val Val Pro Lys Lys Lys Arg Lys
1 5 10 15

Val Val Pro Lys Lys Lys Arg Lys Val Phe Glu Gly Pro Asp Pro Pro
20 25 30

Val

<210> SEQ ID NO 22
<211> LENGTH: 234
<212> TYPE: RNA
<213> ORGANISM: Artificial Sequence
<220> FEATURE:
<223> OTHER INFORMATION: F30-2xdBroccoli

<400> SEQUENCE: 22
uugccaugug uaugugggag acggucgggu ccaucugaga cggucggguc cagauauucg 60
uaucugucga guagagugug ggcucagaug ucgaguagag ugugggcucc cacauacucu 120
gaugauccag acggucgggu ccaucugaga cggucggguc cagauauucg uaucugucga 180
guagagugug ggcucagaug ucgaguagag ugugggcugg aucauucaug gcaa 234

<210> SEQ ID NO 23
<211> LENGTH: 24
<212> TYPE: DNA
<213> ORGANISM: Artificial Sequence
<220> FEATURE:
<223> OTHER INFORMATION: Forword primer of NLS-iRFP coding region

<400> SEQUENCE: 23
ccaatccaca ttccaggagc tatc 24

<210> SEQ ID NO 24
<211> LENGTH: 21
<212> TYPE: DNA
<213> ORGANISM: Artificial Sequence
<220> FEATURE:
<223> OTHER INFORMATION: Riverse primer of NLS-iRFP coding region

<400> SEQUENCE: 24
ctttcgcatt gtgaagccga c 21

<210> SEQ ID NO 25
<211> LENGTH: 21
<212> TYPE: DNA
<213> ORGANISM: Artificial Sequence
<220> FEATURE:
<223> OTHER INFORMATION: Forword primer of PGK1 gene

<400> SEQUENCE: 25

-continued

```
tggacgttaa agggaagcgg g                                                21


<210> SEQ ID NO 26
<211> LENGTH: 25
<212> TYPE: DNA
<213> ORGANISM: Artificial Sequence
<220> FEATURE:
<223> OTHER INFORMATION: Riverse primer of PGK1 gene

<400> SEQUENCE: 26

ggctcataag gactaccgac ttggc                                            25


<210> SEQ ID NO 27
<211> LENGTH: 21
<212> TYPE: DNA
<213> ORGANISM: Artificial Sequence
<220> FEATURE:
<223> OTHER INFORMATION: Forword primer of 18S rRNA

<400> SEQUENCE: 27

cggctaccac atccaaggaa g                                                21


<210> SEQ ID NO 28
<211> LENGTH: 21
<212> TYPE: DNA
<213> ORGANISM: Artificial Sequence
<220> FEATURE:
<223> OTHER INFORMATION: Riverse primer of 18S rRNA

<400> SEQUENCE: 28

tttttcgtca ctacctcccc g                                                21


<210> SEQ ID NO 29
<211> LENGTH: 30
<212> TYPE: RNA
<213> ORGANISM: Artificial Sequence
<220> FEATURE:
<223> OTHER INFORMATION: Linker (30nt)

<400> SEQUENCE: 29

aagguaucug gcggccauag cagcugcgag                                       30


<210> SEQ ID NO 30
<211> LENGTH: 30
<212> TYPE: RNA
<213> ORGANISM: Artificial Sequence
<220> FEATURE:
<223> OTHER INFORMATION: Linker (30nt)

<400> SEQUENCE: 30

aggcacagaa gcggcccaaa gugauagcag                                       30


<210> SEQ ID NO 31
<211> LENGTH: 30
<212> TYPE: RNA
<213> ORGANISM: Artificial Sequence
<220> FEATURE:
<223> OTHER INFORMATION: Linker (30nt)

<400> SEQUENCE: 31

ucaacuuccc gcggcccgcc gccguccuga                                       30


<210> SEQ ID NO 32
<211> LENGTH: 44
<212> TYPE: RNA
<213> ORGANISM: Artificial Sequence
```

-continued

<220> FEATURE:
<223> OTHER INFORMATION: Linker (44nt)

<400> SEQUENCE: 32
auuggucaua ccagaaauug cggccagcaa cgugcgcuuu cacg 44

<210> SEQ ID NO 33
<211> LENGTH: 44
<212> TYPE: RNA
<213> ORGANISM: Artificial Sequence
<220> FEATURE:
<223> OTHER INFORMATION: Linker (44nt)

<400> SEQUENCE: 33
cccccugucu uacucaucug cggccgaaua gagggaguuu aaau 44

<210> SEQ ID NO 34
<211> LENGTH: 44
<212> TYPE: RNA
<213> ORGANISM: Artificial Sequence
<220> FEATURE:
<223> OTHER INFORMATION: Linker (44nt)

<400> SEQUENCE: 34
cgcguguuca ucaaaguggg cggccuagcg uguucaucaa agug 44

<210> SEQ ID NO 35
<211> LENGTH: 66
<212> TYPE: RNA
<213> ORGANISM: Artificial Sequence
<220> FEATURE:
<223> OTHER INFORMATION: Linker (66nt)

<400> SEQUENCE: 35
uggucucuuu gaugucaucc gguugauagc ggccguccgc ccuagauugu uucuaugacc 60
auuaga 66

<210> SEQ ID NO 36
<211> LENGTH: 66
<212> TYPE: RNA
<213> ORGANISM: Artificial Sequence
<220> FEATURE:
<223> OTHER INFORMATION: Linker (66nt)

<400> SEQUENCE: 36
ucaccguggg acggaguaca gaaggagugc ggcccuaaag gcacaagucu aacuaugaac 60
caucau 66

<210> SEQ ID NO 37
<211> LENGTH: 66
<212> TYPE: RNA
<213> ORGANISM: Artificial Sequence
<220> FEATURE:
<223> OTHER INFORMATION: Linker (66nt)

<400> SEQUENCE: 37
ggucuagaac accuaccuua ggccgugugc ggccuuguga cuuacacagu cauuguccac 60
agcccc 66

<210> SEQ ID NO 38
<211> LENGTH: 30
<212> TYPE: RNA
<213> ORGANISM: Artificial Sequence
<220> FEATURE:

<223> OTHER INFORMATION: Linker (30nt)

<400> SEQUENCE: 38
ggaugacgag gcggccuggu uaaaagguag 30

<210> SEQ ID NO 39
<211> LENGTH: 30
<212> TYPE: RNA
<213> ORGANISM: Artificial Sequence
<220> FEATURE:
<223> OTHER INFORMATION: Linker (30nt)

<400> SEQUENCE: 39
cgaucuagga gcggccaguu acgcggugga 30

<210> SEQ ID NO 40
<211> LENGTH: 30
<212> TYPE: RNA
<213> ORGANISM: Artificial Sequence
<220> FEATURE:
<223> OTHER INFORMATION: Linker (30nt)

<400> SEQUENCE: 40
cucacaacaa gcggccguaa cugccuuugu 30

<210> SEQ ID NO 41
<211> LENGTH: 44
<212> TYPE: RNA
<213> ORGANISM: Artificial Sequence
<220> FEATURE:
<223> OTHER INFORMATION: Linker (44nt)

<400> SEQUENCE: 41
gaucgacuga ggauauguug cggccguugg accuggagag uccu 44

<210> SEQ ID NO 42
<211> LENGTH: 44
<212> TYPE: RNA
<213> ORGANISM: Artificial Sequence
<220> FEATURE:
<223> OTHER INFORMATION: Linker (44nt)

<400> SEQUENCE: 42
cuuauaguag uccauggucg cggccuguuu aaacggcuag ucua 44

<210> SEQ ID NO 43
<211> LENGTH: 44
<212> TYPE: RNA
<213> ORGANISM: Artificial Sequence
<220> FEATURE:
<223> OTHER INFORMATION: Linker (44nt)

<400> SEQUENCE: 43
cguaguauac gcgcgugugg cggcccaucg aucuucccgu gcuu 44

<210> SEQ ID NO 44
<211> LENGTH: 66
<212> TYPE: RNA
<213> ORGANISM: Artificial Sequence
<220> FEATURE:
<223> OTHER INFORMATION: Linker (66nt)

<400> SEQUENCE: 44
uauauucggc uaaucaacau cccaacacgc ggccgucgac cgugacagag aacgccugaa 60
uaguaa 66

-continued

<210> SEQ ID NO 45
<211> LENGTH: 66
<212> TYPE: RNA
<213> ORGANISM: Artificial Sequence
<220> FEATURE:
<223> OTHER INFORMATION: Linker (66nt)

<400> SEQUENCE: 45
ucaucuuagc gugcacacac ugguuccagc ggccgugaac gccucgugcg cauuugagug 60
ugcuug 66

<210> SEQ ID NO 46
<211> LENGTH: 66
<212> TYPE: RNA
<213> ORGANISM: Artificial Sequence
<220> FEATURE:
<223> OTHER INFORMATION: Linker (66nt)

<400> SEQUENCE: 46
acucuuuuga acgcccgaua guggcguggc ggcccuuccg gcaauaugua ccugcagaac 60
uaguaa 66

FLUOROGENIC NUCLEIC ACID MOLECULE AND TARGET RNA FLUORESCENT LABELING METHOD

SEQUENCE LISTING

This application includes a Sequence Listing in the ASCII text file in .txt format that is electronically submitted via EFS-Web on Feb. 23, 2022. The ASCII text file contains a sequence listing entitled "10091151.11US9SequenceListing02232022.txt" created on Feb. 23, 2022 and is 8,939 bytes in size. The Sequence Listing contained in this 1009115111US9SequenceListing02232022.txt file is part of the specification and is hereby incorporated by reference herein in its entirety.

CROSS-REFERENCE TO RELATED PATENT APPLICATION

This application claims priority to Japanese Patent Application No. 2018-226743 filed on Dec. 3, 2018, the content of which is incorporated herein by reference.

FIELD OF THE INVENTION

The present invention relates to a fluorogenic nucleic acid molecule for fluorescent labeling of RNA and a method of fluorescently labeling target RNA by using the fluorogenic nucleic acid molecule.

BACKGROUND OF THE INVENTION

In order to better understand how gene expression is controlled at the level of mRNA, there is a strong demand for establishing a method of visualizing spatiotemporal mRNA dynamics in living cells. Generally, mRNA in living cells is visualized using a method of tagging target mRNA with an RNA stem-loop such as MS2 or PP713 and recruiting proteins fused with fluorescent molecules. This technique is applied to track the mRNA movement in the cytoplasm (for example, see Non-Patent Document 1) and to visualize nascent mRNA in the nucleus (for example, see Non-Patent Document 2). However, in visualizing the dynamics of subcellular distribution of tagged mRNA or measuring the expression level of tagged mRNA, the high background of unbound fluorescent proteins often makes it difficult to analyze the results.

As a method of visualizing mRNA in living cells, for example, a method using an RNA aptamer that binds to a specific target molecule in a base sequence-dependent manner is considered as a candidate. Certain RNA aptamers can enhance the fluorescence of small-molecule fluorescent compounds by binding to such compounds (for example, see Non-Patent Documents 3 and 4). These RNA aptamers are also called fluorogenic RNA. Examples of the fluorogenic RNA include Spinach, Broccoli, and derivatives of these binding to small fluorescent molecules of 3,5-difluoro-4-hydroxybenzylidene imidazolinone (DFHBI) families that are analogs of Green Fluorescent Protein (GFP) fluorophores (for example, see Non-Patent Document 5 and Patent Document 1).

CITATION LIST

Patent Document

Patent Document 1: U.S. Pat. No. 9,664,676

Non-Patent Documents

Non-Patent Document 1: Wu et al., Science 2016, vol. 352, p. 1430-1435.

Non-Patent Document 2: Tyagi, Nature Methods, 2009, vol. 6, p. 331-338.

Non-Patent Document 3: Paige et al., Science, 2011, vol. 333, p. 642-646.

Non-Patent Document 4: Filonov et al., Journal of the American Chemical Society, 2014, vol. 136, p. 16299-16308.

Non-Patent Document 5: Filonov et al., Current Protocols in Chemical Biology, 2017, vol. 8(1), p. 1-28.

Non-Patent Document 6: Ketterer et al., Nucleic Acids Research, 2015, vol. 43, p. 9564-9572.

Non-Patent Document 7: Autour et al., Nucleic Acids Research, 2016, vol. 44, p. 2491-2500.

Non-Patent Document 8: Zou et al., Journal of Molecular Evolution, 2015, vol. 81, p. 172-178.

Non-Patent Document 9: Ageely et al., ACS Chemical Biology, 2016, vol. 11, p. 2398-2406.

Non-Patent Document 10: Filonov et al., Chemistry & Biology, 2015, vol. 22, p. 649-660.

Non-Patent Document 11: Filonov et al., Nature Biotechnology, 2011, vol. 29, p. 757-761.

Non-Patent Document 12: Takai, et al., Proceedings of the National Academy of Sciences of the United States of America, 2015, vol. 112, p. 4352-4356.

Non-Patent Document 13: Zuker, Nucleic Acids Research, 2003, Vol. 31, No. 13, p. 3406-3415.

Non-Patent Document 14: Terai et al., Cell structure and Function, 2019, Vol. 44, p. 153-169.

Non-Patent Document 15: Algar et al., Nature Methods, 2019, Vol. 16, p. 815-829.

Non-Patent Document 16: Jepsen et al., NATURE COMMUNICATIONS, 2018, Vol. 9, Article number 18.

Non-Patent Document 17: Han et al., Journal of the American Chemical Society, 2013, Vol. 135, p. 19033-19038.

Non-Patent Document 18: Trachman et al., Trends in Pharmacological Sciences, 2017, vol. 38 (10), p. 928-939.

Non-Patent Document 19: Guo and Bartel, Science, vol. 353 (6306), p. 1382.

SUMMARY OF THE INVENTION

Technical Problem

Theoretically, tagging target mRNA with fluorogenic RNA makes it possible to visualize and quantify the target mRNA in living cells. However, owing to their low fluorescence intensity, all the existing fluorogenic RNAs have not succeeded in visualizing the subcellular mRNA dynamics.

A main object of the present invention is to provide fluorogenic RNA capable of visualizing mRNA in cells, particularly in living mammalian cells, and a target RNA fluorescent labeling method using the fluorogenic RNA.

Solution to the Problem

As a result of intensive studies, the inventors of the present invention have found that in a case where a plurality of fluorogenic RNAs incorporated into scaffold RNAs is tandemly linked via linker sequences to form a nucleic acid molecule, the nucleic acid molecule can markedly enhance the intensity of the generated fluorescence when binding to fluorescent molecules. Furthermore, the inventors have found that in a case where target RNA is labeled with the nucleic acid molecule, the target RNA in living cells can be visualized. Based on these findings, the inventors have accomplished the present invention.

That is, a fluorogenic nucleic acid molecule, a target RNA fluorescent labeling method, a vector, a linker sequence-designing method, a fluorescence signal detection method, and a screening method according to the present invention are as described in the following (1) to (23).

(1) A fluorogenic nucleic acid molecule, containing a base sequence having 2 or more fluorescent molecule-binding regions linked via a linker sequence, in which 1 or more fluorescent molecule-binding aptamer sequences are inserted into a scaffold sequence of each of the fluorescent molecule-binding regions.

(2) The fluorogenic nucleic acid molecule described in (1), in which a length of the linker sequence is 20 nt or more.

(3) The fluorogenic nucleic acid molecule described in (1) or (2), in which the linker sequence does not form a specific 3-dimensional structure.

(4) The fluorogenic nucleic acid molecule described in (3), in which 2 or more of the fluorescent molecule-binding aptamer sequences are inserted into the scaffold sequence of each of the fluorescent molecule-binding regions.

(5) The fluorogenic nucleic acid molecule described in (4), in which the fluorescent molecule-binding regions each have a structure in which least 2 loop structures in a single-stranded nucleic acid molecule forming a stem-loop structure containing 2 or more loop structures are substituted with the fluorescent molecule-binding aptamer sequences.

(6) The fluorogenic nucleic acid molecule described in any one of (1) to (5), in which the fluorescent molecule-binding aptamer sequences each contain a base sequence of a single-stranded nucleic acid molecule forming a stem-loop structure flanked by G-quadruplex structures, and the stem-loop structure consists of a 4 to 6 bp stem structure and a 4 bp loop structure.

(7) The fluorogenic nucleic acid molecule described in any one of (1) to (5), in which the fluorescent molecule-binding aptamer sequences are Broccoli, Broccoli3, or dBroccoli.

(8) The fluorogenic nucleic acid molecule described in any one of (1) to (5), in which the fluorescent molecule-binding regions each consist of a base sequence represented by SEQ ID NO: 16 or 17.

(9) The fluorogenic nucleic acid molecule described in any one of (1) to (8), in which the linker sequence consists of a base sequence represented by any of SEQ ID NOS: 18 to 20.

(10) The fluorogenic nucleic acid molecule described in any one of (1) to (9), which contains 4 or more of the fluorescent molecule-binding aptamer sequences.

(11) The fluorogenic nucleic acid molecule described in any one of (1) to (10), in which fluorescent molecules binding to the fluorescent molecule-binding aptamer sequences are fluorescent molecules of a DFHBI family.

(12) A target RNA fluorescent labeling method that is a method of fluorescently labeling target RNA, including directly or indirectly linking the fluorogenic nucleic acid molecule described in any one of (1) to (11) to a target RNA, and then bringing the fluorogenic nucleic acid molecule into contact with fluorescent molecules to which the fluorescent molecule-binding aptamer sequences in the fluorogenic nucleic acid molecule bind.

(13) The target RNA fluorescent labeling method described in (12), in which the target RNA is a transcript of a target gene, the fluorescent molecules to which the fluorescent molecule-binding aptamer sequences in the fluorogenic nucleic acid molecule bind are introduced into a cell in which a base sequence encoding the fluorogenic nucleic acid molecule is incorporated into a 3' untranslated region of the target gene, so that the fluorescent molecules bind to the transcript of the target gene.

(14) A target RNA fluorescent labeling method that is a method of fluorescently labeling a target RNA, the method including mixing a sample containing a target RNA with a nucleic acid molecule which is obtained by directly or indirectly linking a probe to be hybridized with a part of the target RNA to the fluorogenic nucleic acid molecule described in any one of (1) to (11) and fluorescent molecules to which the fluorescent molecule-binding aptamer sequences in the nucleic acid molecule bind.

(15) A vector including a promoter that controls expression of a foreign gene, a restriction enzyme site that is downstream side of the promoter and used for inserting a coding region of the foreign gene, and a 3' untranslated region that is downstream side of the restriction enzyme site, in which the 3' untranslated region contains a base sequence encoding the fluorogenic nucleic acid molecule described in any one of (1) to (11).

(16) A linker sequence-designing method that is a method of designing a linker sequence in a fluorogenic nucleic acid molecule containing a base sequence having 2 or more fluorescent molecule-binding regions which each have 1 or more fluorescent molecule-binding aptamer sequences inserted into a scaffold sequence and are linked via the linker sequence, the method including designing a linker sequence so that in a case where a candidate linker sequence is linked to upstream and downstream side of each of the fluorescent molecule-binding regions to prepare an RNA sequence used as an RNA sequence for evaluation, a result of prediction of a 3-dimensional structure of the fluorescent molecule-binding region in the RNA sequence for evaluation is identical to a result of prediction of a 3-dimensional structure of an RNA sequence consisting only of the fluorescent molecule-binding region, and the candidate linker sequence portion is not predicted to have a 3-dimensional structure.

(17) The linker sequence-designing method described in (16), in which the candidate linker sequence is a sequence prepared by adding a random RNA sequence to a restriction enzyme site.

(18) The linker sequence-designing method described in (16) or (17), in which a length of the candidate linker sequence is 20 nt or more and 80 nt or less.

(19) A method of detecting a fluorescence signal emitted from a fluorescent molecule bound to a fluorogenic nucleic acid molecule, the method including binding a fluorescent molecule of a DFHBI family to the fluorogenic nucleic acid molecule described in (11), then continuously illuminating the fluorogenic nucleic acid molecule for a certain period of time with excitation light for the fluorescent molecule of the DFHBI family, and detecting a value of brightness obtained by subtracting a value of brightness of a fluorescence signal at an illumination end point from a value of brightness of a fluorescence signal at an illumination start point as a fluorescence signal emitted from the fluorescent molecule of the DFHBI family bound to the fluorogenic nucleic acid molecule.

(20) The method of detecting a fluorescence signal emitted from a fluorescent molecule bound to a fluorogenic nucleic acid molecule described in (19), further including repeatedly illuminating the fluorogenic nucleic acid molecule bound to the fluorescent molecule of the DFHBI family with the excitation light in multiple illumination cycles each consisting of continuous illumination for a certain period of time followed by interruption of illumination for a certain period of time, detecting a fluorescence signal at the illumination start point of the continuous illumination and a fluorescence signal at the illumination end point for each illumination cycle, averaging values of brightness of fluorescence signals at the illumination start point of the continuous illumination detected for all illumination cycles, averaging values of brightness of fluorescence signals at the illumination end point of the continuous illumination detected for all illumination cycles, and detecting a value of brightness obtained by subtracting the averaged value of brightness of fluorescence signals at the illumination end point from the averaged value of brightness of fluorescence signals at the illumination start point as a fluorescence signal of the fluorescent molecule of the DFHBI family bound to the fluorogenic nucleic acid molecule.

(21) A screening method that is a method of screening an inhibitor inhibiting binding of the fluorogenic nucleic acid molecule described in any one of (1) to (11) to a fluorescent molecule to which the fluorescent molecule-binding aptamer sequences in the fluorogenic nucleic acid molecule bind, the method comprising:

incorporating a candidate substance of the inhibitor into a reaction system in which the fluorogenic nucleic acid molecule and the fluorescent molecule coexist, measuring a fluorescence signal emitted from the fluorescent molecule, and selecting the candidate substance as the inhibitor in a case where a value of brightness obtained by the measurement is lower than a value of brightness of a fluorescence signal emitted from the fluorescent molecule bound to the fluorogenic nucleic acid molecule in the absence of the candidate substance.

(22) The screening method described in (21), in which each of the fluorescent molecule-binding aptamer sequences in the fluorogenic nucleic acid molecule is a base sequence of a single-stranded nucleic acid molecule forming a stem-loop structure flanked by G-quadruplex structures, the fluorescent molecule is a fluorescent molecule of a DFHBI family, and the inhibitor has an activity of unfolding the G-quadruplex structures.

(23) The screening method described in (22), further including introducing the fluorescent molecule into a cell co-expressing the fluorogenic nucleic acid molecule and the candidate protein, measuring fluorescence signals, and selecting the candidate protein as a substance having an activity of unfolding the G-quadruplex structures in a case where a value of brightness obtained by the measurement is lower than a fluorescence signal obtained by introducing the fluorescent molecule into a cell expressing only the fluorogenic nucleic acid molecule.

Advantageous Effects of the Invention

The fluorogenic nucleic acid molecule according to the present invention has a structure in which fluorescent molecule-binding regions each having 1 or more fluorescent molecule-binding aptamer sequences inserted into a scaffold sequence are tandemly linked. Depending on the number of fluorescent molecule-binding regions to be linked, the fluorogenic nucleic acid molecule according to the present invention can enhance the intensity of fluorescence generated when binding to a fluorescent molecule. Therefore, the fluorogenic nucleic acid molecule according to the present invention having a sufficient number of fluorescent molecule-binding regions linked to each other is useful as a visualization tool for mRNA in living cells.

DETAILED DESCRIPTION OF THE INVENTION

Figure 1:
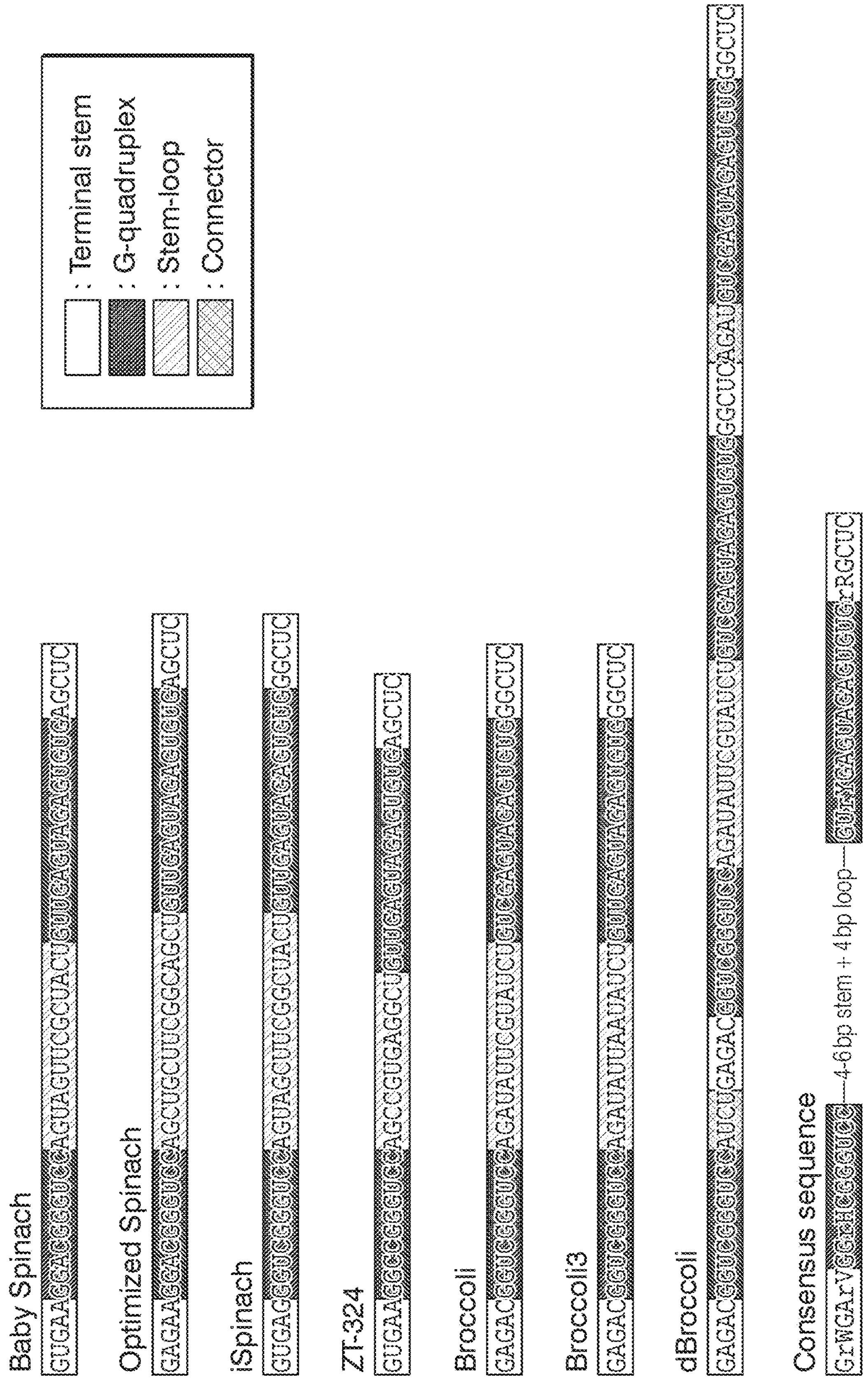
FIG. 1 is a schematic diagram of fluorescent molecule-binding aptamer sequences to be paired with fluorescent molecules of the DFHBI family.

In the present invention and the present specification, "fluorescent molecule-binding aptamer" means an RNA aptamer that markedly enhances fluorescence generated from a specific fluorescent molecule by binding to the fluorescent molecule. "Fluorescent molecule-binding aptamer sequence" means a base sequence of such an RNA aptamer. Furthermore, "fluorescent molecule to be paired with a fluorescent molecule-binding aptamer sequence" means a fluorescent molecule that generates markedly enhanced fluorescence by binding to such an RNA aptamer.

Fluorogenic Nucleic Acid Molecule

The fluorogenic nucleic acid molecule according to the present invention has a structure in which 2 or more fluorescent molecule-binding regions each having 1 or more fluorescent molecule-binding aptamer sequences inserted in a scaffold sequence are tandemly linked. In the present invention, the number of fluorescent molecule-binding aptamer sequences contained in each fluorescent molecule-binding region may be 1 or 2 or more. The fluorogenic nucleic acid molecule according to the present invention has at least 2 fluorescent molecule-binding regions, and a large number of fluorescent molecules to be paired bind to one fluorogenic nucleic acid molecule. Therefore, compared to fluorogenic nucleic acid molecules each having only 1 fluorescent molecule-binding region, the fluorogenic nucleic acid molecule according to the present invention emits fluorescence with higher intensity in the presence of a fluorescent molecule.

The number of fluorescent molecule-binding regions contained in the fluorogenic nucleic acid molecule according to the present invention is not particularly limited as long as it is 2 or more. The larger the number of fluorescent molecule-binding regions contained in one molecule, the larger the number of fluorescent molecule-binding aptamer sequences present in one molecule, which leads to the increase in the number of fluorescent molecules to be paired binding to the nucleic acid molecule. That is, the intensity of fluorescence generated when the fluorogenic nucleic acid molecule binds to a fluorescent molecule to be paired increases depending on the number of fluorescent molecule-binding regions to be linked. In a case where the fluorogenic nucleic acid molecule according to the present invention is used for labeling a molecule such as RNA in a living cell, an appropriate number of fluorescent molecule-binding regions are tandemly linked via a linker sequence so that the number of fluorescent molecule-binding aptamer sequences contained in one fluorogenic nucleic acid molecule is 4 or more, preferably 8 or more, more preferably 10 or more, and even more preferably 12 or more. The upper limit of the number of fluorescent molecule-binding regions contained in the fluorogenic nucleic acid molecule according to the present invention is not particularly limited. Considering stability in living cells and the like, the number of fluorescent molecule-binding regions in one fluorogenic nucleic acid molecule is preferably 10 or less, and more preferably 8 or less. For example, a fluorogenic nucleic acid molecule in which 6 fluorescent molecule-binding regions each containing 2 fluorescent molecule-binding aptamer sequences are tandemly linked via a linker sequence generates fluorescence with sufficient intensity when binding to a fluorescent molecule to be paired. Therefore, such a fluorogenic nucleic acid molecule is suited for fluorescent labeling of molecules in living cells, particularly, RNA such as mRNA.

The fluorescent molecule-binding aptamer sequences contained in the fluorogenic nucleic acid molecule according to the present invention is not particularly limited, and can be appropriately selected depending on the type of fluorescent molecule to be used. The fluorescent molecule-binding aptamer sequences contained in the fluorogenic nucleic acid molecule according to the present invention are preferably fluorescent molecule-binding aptamer sequences to be paired with a small fluorescent molecule of the DFHBI family. Examples of "fluorescent molecule of the DFHBI family" (hereinafter, called "DFHBI family molecule" in some cases) include DFHBI, DFHBI-1T ((Z)-4-(3,5-difluoro-4-hydroxybenzylidene))-2-methyl-1-(2,2,2-trifluoroethyl)-1H-imidazol-5(4H)-one), DFHO (4-(3,5-difluoro-4-hydroxybenzylidene)-1-methyl-5-oxo-4,5-dihydro-1H-imidazole-2-carbaldehyde), and the like.

Examples of "fluorescent molecule-binding aptamer sequence to be paired with a DFHBI family molecule" (hereinafter, called "DFHBI-binding aptamer sequence" in some cases) include those having, as a consensus sequence, a base sequence having a structure in which a stem-loop structure consisting of a 4 to 6 bp stem structure and a 4 bp loop structure is flanked by G-quadruplex structures. In the consensus sequence, the base sequences of the G-quadruplex structure portions and the terminal stem are not particularly limited. For example, the 5'-end side and the 3'-end side of the stem-loop structure can have the base sequences shown in FIG. 1 (5'-end side of stem-loop structure: SEQ ID NO: 1 (5'-GrWGArVGGrHCGGGUCC-3'), 3'-end side of stem-loop structure: SEQ ID NO: 2 (5'-GUrYGAGUAGAGUGUGrRGCUC-3')). In FIG. 1, "rW" represents A (adenine) or U (uracil), "rV" represents A, C (cytosine), or G (guanine), "rH" represents A, U, or C, "rY" represents U or C, and "rR" represents A or G.

The base sequence of the stem-loop structure portion in the consensus sequence is not particularly limited, and examples thereof include a base sequence represented by any of SEQ ID NOS: 3 to 5 having a 5 bp stem structure and a base sequence represented by SEQ ID NO: 6 or 7 having a 6 bp stem structure. In the fluorescent molecule-binding aptamer sequences contained in the fluorogenic nucleic acid molecule according to the present invention, the base sequence of the stem-loop structure portion is preferably a base sequence represented by SEQ ID NO: 3 or 6.

TABLE 1

| | Sequence | SEQ ID NO |
|---|---|---|
| 5 bp stem structure | AGAUAUUAAUAUCU | 3 |
| | AGAUAUUCGUAUCU | 4 |
| | AGUAGUUCGCUACU | 5 |
| 6 bp stem structure | AGUAGCUUCGGCUACU | 6 |
| | AGCUGCUUCGGCAGCU | 7 |

Specific examples of the fluorescent molecule-binding aptamer sequences having the above consensus sequence include Spinach (Baby Spinach) (SEQ ID NO: 8, Non-Patent Document 3), Optimized Spinach (SEQ ID NO: 9, Non-Patent Document 6), iSpinach (SEQ ID NO: 10, Non-Patent Document 7), ZT-324 (SEQ ID NO: 11, Non-Patent Document 8), Broccoli (SEQ ID NO: 12, Non-Patent Document 4), Broccoli3 (SEQ ID NO: 13, Non-Patent Document 9), dBroccoli (SEQ ID NO: 14, Non-Patent Document 4), and the like. FIG. 1 is a schematic diagram of these sequences.

In the present invention, the fluorescent molecule-binding region consists of a single-stranded nucleic acid structure in which 1 or more fluorescent molecule-binding aptamer sequences are inserted into a scaffold sequence. The scaffold sequence is not particularly limited, as long as it is a base sequence of single-stranded RNA that can function as a scaffolding without impairing the fluorogenicity of single-stranded RNA consisting of the sequence in a case where the fluorescent molecule-binding aptamer sequence is inserted into the scaffold sequence. The scaffold sequence may be, for example, a base sequence of a single-stranded nucleic acid molecule forming a stem-loop structure. Examples of the scaffold sequence include tRNA and a three-way junction motif derived from various organisms, variants of these, and the like. Among these, the F30 scaffold sequence (SEQ ID NO: 15, Non-Patent Document 10) is preferable, which is a variant of the three-way junction motif derived from the Phi29 virus. RNA consisting of the F30 scaffold sequence is not recognized by the cell nuclease. Therefore, a fluorogenic nucleic acid molecule having a fluorescent molecule-binding region in which a fluorescent molecule-binding aptamer sequence is inserted into the portion of loop structure of the F30 scaffold sequence is extremely stable in cells.

The insertion of the fluorescent molecule-binding aptamer sequence into the scaffold sequence forming a stem-loop structure can be performed, for example, by substituting the portion of loop structure in the stem-loop structure with the fluorescent molecule-binding aptamer sequence. In a case where one fluorescent molecule-binding region contains 2 or more fluorescent molecule-binding aptamer sequences, the fluorescent molecule-binding region has, for example, a structure in which at least 2 loop structures in a single-stranded nucleic acid molecule forming a stem-loop structure containing 2 or more loop structures are substituted with the fluorescent molecule-binding aptamer sequences.

The fluorescent molecule-binding region of the fluorogenic nucleic acid molecule according to the present invention is preferably a region in which the DFHBI-binding aptamer sequence is inserted into 1 or 2 loop structures in the F30 scaffold sequence, and more preferably a region in which the fluorescent molecule-binding aptamer sequence containing the consensus sequence shown in FIG. 1 is inserted into 1 or 2 loop structures in the F30 scaffold sequence. Particularly, in view of higher detection sensitivity to RNA in living cells, the fluorescent molecule-binding region is preferably a region established by inserting the base sequence of Baby Spinach, Optimized Spinach, iSpinach, ZT-324, Broccoli, Broccoli3, or dBroccoli into 1 or 2 loop structures of the F30 scaffold sequence, more preferably a region established by inserting the base sequence of Broccoli3 into 1 loop structure in the F30 scaffold sequence (SEQ ID NO: 16) or a region established by inserting the base sequence of Broccoli3 into 2 loop structures in the F30 scaffold sequence (SEQ ID NO: 17), and particularly preferably a region established by inserting the base sequence of Broccoli3 into 2 loop structures in the F30 scaffold sequence. In the table, the inserted base sequence of Broccoli3 is underlined. "Fluorescent molecule-binding aptamer sequence in which 1 fluorescent molecule-binding aptamer sequence is inserted into the F30 scaffold sequence" can be prepared by substituting the underlined portion of SEQ ID NO: 16 with the fluorescent molecule-binding aptamer sequence. "Fluorescent molecule-binding aptamer sequence in which 2 fluorescent molecule-binding aptamer sequences are inserted into the F30 scaffold sequence" can be prepared by substituting the underlined portion of SEQ ID NO: 17 with the fluorescent molecule-binding aptamer sequence.

TABLE 2

| | Sequence | SEQ ID NO |
|---|---|---|
| F30-Broccoli3 | UUGCCAUGUGUAUGUGGGAGACGGU<br>CGGGUCCAGAUAUUAAUAUCUGUUG<br>AGUAGAGUGUGGGCUCCCACAUACU<br>CUGAUGAUCCUUCGGGAUCAUUCAU<br>GGCAA | 16 |
| F30-2 × Broccoli3 | UUGCCAUGUGUAUGUGGGAGACGGU<br>CGGGUCCAGAUAUUAAUAUCUGUUG<br>AGUAGAGUGUGGGCUCCCACAUACU<br>CUGAUGAUCCGAGACGGUCGGGUCC<br>AGAUAUUAAUAUCUGUUGAGUAGAG<br>UGUGGGCUCGGAUCAUUCAUGGCAA | 17 |

The fluorogenic nucleic acid molecule according to the present invention contains a base sequence in which 2 or more fluorescent molecule-binding regions are linked via a linker sequence. The linker sequence is not particularly limited as long as it does not impair the fluorogenicity of the fluorescent molecule-binding aptamer sequences contained in the fluorogenic nucleic acid molecule. For example, for the convenience of construction of the fluorogenic nucleic acid molecule, labeling of target RNA, and the like, the linker sequence may include a functional sequence such as a restriction enzyme sequence. The linker sequence can be designed, for example, using RNA 3-dimensional structure prediction software so that the linker sequence does not inhibit the formation of a 3-dimensional structure of the fluorescent molecule-binding aptamer sequences in the fluorescent molecule-binding region. Examples of the RNA 3-dimensional structure prediction software include software such as "mFold" (Non-Patent Document 13) that predicts a 3-dimensional structure minimizing free energy.

The phenomenon in which Forster Resonance Energy Transfer (FRET) occurs between fluorescent molecules of the same type is called homo-FRET. The fluorescent molecules in which homo-FRET occurs show brightness reduction or emit fluorescence for a shorter period of time (Non-Patent Documents 14 and 15). In addition, the efficiency of homo-FRET is affected by the distance or positional relationship between fluorescent molecules (Non-Patent Document 16). In order to avoid the FRET-induced reduction of fluorescence efficiency, the linker sequence in the fluorogenic nucleic acid molecule according to the present invention is preferably designed so that FRET does not occur between fluorescent molecules binding to the fluorescent molecule-binding aptamer sequences in the fluorescent molecule-binding regions linked via the linker sequence. For example, the linker sequence preferably consists of a base sequence that has a length of 20 nt or more and is unlikely to have a specific 3-dimensional structure. In a case where the length of the linker sequence is preferably 20 nt or more, more preferably 22 nt or more, and even more preferably 24 nt or more, the fluorescent molecules binding to the plurality of fluorescent molecule-binding aptamer sequences in the fluorogenic nucleic acid molecule can be spaced apart such that FRET is unlikely to occur. Furthermore, the linker sequence is preferably a flexible sequence that does not have a specific 3-dimensional structure for the following reason. In a case where the linker sequence is flexible, the fluorescent molecules binding to the plurality of fluorescent molecule-binding aptamer sequences in the fluorogenic nucleic acid molecule are not in a fixed positional relationship that can cause FRET, and FRET is unlikely to occur. In addition to homo-FRET, there are mechanisms that cause fluorescence quenching by the interaction between neighboring fluorescent molecules. The flexible linker sequence is also expected to inhibit these mechanisms.

In a case where the linker sequence is too long, the fluorescent molecules binding to the plurality of fluorescent molecule-binding aptamer sequences in the fluorogenic nucleic acid molecule are spaced apart too much, and the fluorogenic nucleic acid molecule itself becomes too long. Therefore, the length of the linker sequence is preferably 100 nt or less, more preferably 90 nt or less, and even more preferably 80 nt or less.

The linker sequence consisting of a base sequence that has a length of 20 nt or more and is unlikely to have a specific 3-dimensional structure is preferably designed, so that in a case where the linker sequence is linked to upstream side (5'-end side) and downstream side (3'-end side) of one fluorescent molecule-binding region to prepare an RNA sequence used as an RNA sequence for evaluation, a result of prediction of a 3-dimensional structure of the fluorescent molecule-binding region in the RNA sequence for evaluation is identical to a result of prediction of a 3-dimensional structure of an RNA sequence consisting only of the fluorescent molecule-binding region, and the linker sequence portion is not predicted to have a 3-dimensional structure. More specifically, the linker sequence can be designed by the following method, for example. First, as a candidate linker sequence, a random RNA sequence is designed which has a length of 20 nt or more and preferably has a length of 20 to 80 nt. Then, the designed candidate linker sequence is linked to upstream and downstream side of 1 fluorescent molecule-binding region to design an RNA sequence used as an RNA sequence for evaluation, and the 3-dimensional structure of the RNA sequence for evaluation is predicted. The 3-dimensional structure prediction of single-stranded RNA can be performed using RNA 3-dimensional structure prediction software, such as “mFold”, for predicting a 3-dimensional structure minimizing free energy. In a case where the 3-dimensional structure prediction of the RNA sequence for evaluation reveals that the result of prediction of the 3-dimensional structure of the fluorescent molecule-binding region is identical to the result of prediction of the 3-dimensional structure of an RNA sequence consisting only of the fluorescent molecule-binding region, and the candidate linker sequence portion is not predicted to have a 3-dimensional structure, the candidate linker sequence is evaluated as being preferable as a linker sequence in the fluorogenic nucleic acid molecule according to the present invention. Compared to a linker sequence for which the 3-dimensional structure prediction of the RNA sequence for evaluation reveals that the result of prediction of the 3-dimensional structure of the fluorescent molecule-binding region is different from the result of prediction of the 3-dimensional structure of an RNA sequence consisting only of the fluorescent molecule-binding region or a linker sequence for which the 3-dimensional structure prediction reveals that the candidate linker sequence portion is predicted to have a 3-dimensional structure, a linker sequence for which the 3-dimensional structure prediction reveals that the result of prediction of the 3-dimensional structure of the fluorescent molecule-binding region is identical to the result of prediction of the 3-dimensional structure of an RNA sequence consisting only of the fluorescent molecule-binding region and the candidate linker sequence portion is not predicted to have a 3-dimensional structure less likely to cause FRET-induced reduction of fluorescent brightness or the like. In a case where a plurality of candidate linker sequences is obtained which is evaluated as being preferable as the linker sequence in the fluorogenic nucleic acid molecule according to the present invention, a candidate linker sequence further reducing free energy of the RNA sequence for evaluation can be evaluated as being more preferable as a linker sequence in the fluorogenic nucleic acid molecule according to the present invention. It is preferable to design the fluorogenic nucleic acid molecule by using, as a linker sequence, a candidate linker sequence for which the result of prediction of the 3-dimensional structure of the fluorescent molecule-binding region in the RNA sequence for evaluation is identical to the result of prediction of the 3-dimensional structure of an RNA sequence consisting only of the fluorescent molecule-binding region and the candidate linker sequence portion is not predicted to have a 3-dimensional structure.

Candidate linker sequences can be designed, for example, using four types of RNA, AUGC, by a general method such as the RANDBETWEEN function used for creating a random letter string. In addition, for the convenience of synthesizing the fluorogenic nucleic acid molecule, a linker sequence obtained by incorporating a functional sequence such as a restriction enzyme site into a random base sequence can be used as a candidate linker sequence.

In a case where the fluorescent molecule-binding regions in the fluorogenic nucleic acid molecule according to the present invention are each constructed by inserting the base sequence of Baby Spinach, Optimized Spinach, iSpinach, ZT-324, Broccoli, Broccoli3, or dBroccoli into 1 or 2 loop structures in the F30 scaffold sequence, as a linker sequence linking the fluorescent molecule-binding regions, a base sequence having a length of 25 to 75 nt is preferable, a base sequence having a length of 30 to 70 nt is more preferable, and a random sequence having a length of 30 to 70 nt and containing a restriction enzyme recognition sequence near the center is even more preferable. Particularly, in a case where the fluorescent molecule-binding regions are each constructed by inserting the base sequence of Broccoli3 into 1 or 2 loop structures in the F30 scaffold sequence, as a linker sequence linking the fluorescent molecule-binding regions, a base sequence represented by SEQ ID NOS: 18 and 29 to 31 (having a length of 30 nt), SEQ ID NOS: 19 and 32 to 34 (having a length of 44 nt), or SEQ ID NOS: 20 and 35 to 37 (having a length of 66 nt) is preferable, a base sequence represented by SEQ ID NO: 18 (having a length of 30 nt), SEQ ID NO: 19 (having a length of 44 nt), or SEQ ID NO: 20 (having a length of 66 nt) is more preferable, and a base sequence represented by SEQ ID NO: 16 is particularly preferable.

TABLE 3

| | Sequence | SEQ ID NO |
|---|---|---|
| 30 nt linker | CAGUGGGGCAGCGGCCGGUCGUCUGGGGGA | 18 |
| | AAGGUAUCUGGCGGCCAUAGCAGCUGCGAG | 29 |
| | AGGCACAGAAGCGGCCCAAAGUGAUAGCAG | 30 |
| | UCAACUUCCCGCGGCCCGCCGCCGUCCUGA | 31 |
| 44 nt linker | CAGACGUUGUCCGCCUUGUGCGGCCGAUCGACUGAG GAUAUGAA | 19 |
| | AUUGGUCAUACCAGAAAUUGCGGCCAGCAACGUGCG CUUUCACG | 32 |
| | CCCCCUGUCUUACUCAUCUGCGGCCGAAUAGAGGGA GUUUAAAU | 33 |

TABLE 3-continued

| | Sequence | SEQ ID NO |
|---|---|---|
| | CGCGUGUUCAUCAAAGUGGGCGGCCUAGCGUGUUCA UCAAAGUG | 34 |
| 66 nt linker | GGAUCAUUCAUGGCAAUCUAGCACCUUCGCGGCCGA ACAUACAACUGCUUGCCAUGUGUAUGUGGG | 20 |
| | UGGUCUCUUUGAUGUCAUCCGGUUGAUAGCGGCCGU CCGCCCUAGAUUGUUUCUAUGACCAUUAGA | 35 |
| | UCACCGUGGGACGGAGUACAGAAGGAGUGCGGCCCU AAAGGCACAAGUCUAACUAUGAACCAUCAU | 36 |
| | GGUCUAGAACACCUACCUUAGGCCGUGUGCGGCCUU GUGACUUACACAGUCAUUGUCCACAGCCCC | 37 |

The fluorogenic nucleic acid molecule according to the present invention is an RNA molecule having a single-stranded structure. In the RNA constituting the fluorogenic nucleic acid molecule according to the present invention, all RNA constituting the molecule may be natural nucleotides, or a part or all of RNA constituting the molecule may be nucleic acid analogs capable of forming a nucleotide chain or a base pair just as natural nucleotides. Examples of the nucleic acid analogs include Bridged nucleic acid (BNA), a nucleotide formed by substitution of an oxygen atom at the 4' position in a natural nucleotide with a sulfur atom, a nucleotide formed by substitution of a hydroxyl group at the 2' position in a natural nucleotide with a methoxy group, Hexitol Nucleic Acid (HNA), peptide nucleic acid (PNA), and the like. Furthermore, a part of RNA constituting the fluorogenic nucleic acid molecule according to the present invention may be DNA.

The fluorogenic nucleic acid molecule according to the present invention may have other regions in addition to the region in which the fluorescent molecule-binding regions are linked via a linker sequence, as long as the fluorogenicity of the region is not impaired. Examples of such other regions include a region that interacts with a substance other than the fluorescent molecule to be paired, and the like. In addition, the fluorogenic nucleic acid molecule according to the present invention may be linked to a substance fluorescently labeled by the fluorescent molecule to be paired, directly or via an appropriate linker.

By binding to the fluorescent molecule to be paired, the fluorogenic nucleic acid molecule according to the present invention generates intense fluorescence. Therefore, the fluorogenic nucleic acid molecule according to the present invention can be used for fluorescent labeling of various substances including biomolecules. Specifically, the fluorogenic nucleic acid molecule according to the present invention is directly or indirectly bonded to a molecule of interest to be fluorescently labeled (target molecule) and then bonded to a fluorescent molecule to be paired.

Target RNA Fluorescent Labeling Method

By directly or indirectly bonding the fluorogenic nucleic acid molecule according to the present invention to a target RNA (RNA of interest to be fluorescently labeled), it is possible to fluorescently label the target RNA. Specifically, the fluorogenic nucleic acid molecule according to the present invention is directly or indirectly linked to the target RNA, and then brought into contact with fluorescent molecules to which the fluorescent molecule-binding aptamer sequences in the fluorogenic nucleic acid molecule bind. The target RNA of the fluorescent labeling method may be intracellular RNA or extracellular RNA.

In a case where the target RNA is a transcript of a target gene, it is preferable to bond the transcript of the target gene to the fluorogenic nucleic acid molecule according to the present invention. For example, the fluorogenic nucleic acid molecule according to the present invention is incorporated into the 3' untranslated region of the target gene. As a result, the target gene is transcribed together with the fluorogenic nucleic acid molecule according to the present invention added to the 3'-end side thereof. Therefore, the obtained transcript can be fluorescently labeled with the fluorescent molecule to be paired. Specifically, fluorescent molecules to which the fluorescent molecule-binding aptamer sequences in the fluorogenic nucleic acid molecule according to the present invention bind are introduced into a cell in which a base sequence encoding the fluorogenic nucleic acid molecule is incorporated into the 3' untranslated region of the target gene, so that the transcript of the target gene binds to the fluorescent molecules. By the direct incorporation of the fluorogenic nucleic acid molecule according to the present invention into the 3' untranslated region of the target gene, during gene expression in the cell, mRNA of the target gene can be visualized by fluorescence in the entire process of transcription initiation, translation, and the subsequent degradation and detected in real time, which makes it possible to quantify the subcellular target gene expression level. Particularly, because the fluorogenic nucleic acid molecule according to the present invention has high fluorogenicity and generates intense fluorescence signals, subcellular localization of mRNA labeled with the fluorogenic nucleic acid molecule can be analyzed in real time by microscopic image analysis.

In a case where the target gene is an endogenous gene, a DNA fragment encoding the fluorogenic nucleic acid molecule according to the present invention is inserted into the 3' untranslated region within the target gene region in the chromosome. The DNA fragment insertion can be performed by conventional methods using various genetic engineering techniques such as gene editing methods known in the related art.

In a case where a foreign gene is to be introduced into and expressed in a cell, generally, a vector combined with an expression cassette for expressing the foreign gene is introduced into the cell. The expression cassette is a DNA fragment necessary for expressing the foreign gene, and includes at least a coding region of the gene and a promoter that controls the expression of the gene. The expression cassette preferably further includes a 5' untranslated region, a 3' untranslated region, and a terminator.

In a case where the target gene is a foreign gene, a DNA fragment encoding the fluorogenic nucleic acid molecule according to the present invention is inserted in advance into the 3' untranslated region in the target gene expression cassette. Introducing the expression cassette, in which the fluorogenic nucleic acid molecule according to the present invention is inserted into the 3' untranslated region, into a cell allows the target gene to be transcribed together with the fluorogenic nucleic acid molecule according to the present invention added to the 3'-end side. The target gene expression cassette may be introduced into the extranuclear region of the cell or incorporated into the chromosome in the nucleus. The target gene expression cassette can be prepared by incorporating the coding region of the target gene into an expression cassette known in the related art. The target gene expression cassette can be introduced into cells by conventional methods using various gene recombination techniques known in the related art such as lipofection, electroporation, and homologous recombination.

Generally, a vector combined with a foreign gene expression cassette is prepared from a cloning vector having a restriction enzyme site instead of the coding region of the foreign gene. Specifically, the cloning vector has a promoter that controls the expression of the foreign gene, a restriction enzyme site that is downstream side of the promoter and used for inserting the coding region of the foreign gene, and a 3' untranslated region that is downstream side of the restriction enzyme site. By incorporating a DNA fragment consisting of a coding region of a foreign gene into the restriction enzyme site of the cloning vector, a foreign gene expression vector is obtained.

The vector obtained by incorporating in advance a base sequence encoding the fluorogenic nucleic acid molecule according to the present invention into the 3' untranslated region of the cloning vector is useful for obtaining a transcript in which the fluorogenic nucleic acid molecule is added to the 3'-end side. Incorporating a DNA fragment of the coding region of the target gene into the restriction enzyme site of the vector makes it possible to prepare a target gene expression vector for obtaining a cell in which the target gene is transcribed together with the fluorogenic nucleic acid molecule according to the present invention added to the 3'-end side. This vector can be prepared, for example, by incorporating a base sequence encoding the fluorogenic nucleic acid molecule according to the present invention into the 3' untranslated region of a commercially available expression vector into which a DNA fragment of a coding region of a target gene is to be inserted to prepare a target gene expression vector.

Fluorescent labeling of target RNA can also be performed using a fluorogenic nucleic acid molecule with a probe that is directly or indirectly linked to the end of the molecule and is to be hybridized with a part of target RNA. The probe can be designed, synthesized, and bonded to the end of the fluorogenic nucleic acid molecule by conventional methods. A sample containing target RNA is mixed with the fluorogenic nucleic acid molecule to which the probe is linked and a fluorescent molecule to be paired with a fluorescent molecule-binding aptamer sequence in the fluorogenic nucleic acid molecule. As a result, the target RNA is labeled with the fluorescent molecule.

The structure of a DFHBI family molecule such as Baby Spinach changes in a photo-dependent manner. The fluorescent molecule after the structural change does not bind to single-stranded RNA consisting of a DFHBI-binding aptamer sequence. Therefore, in a case where a complex of a DFHBI family molecule and a fluorogenic nucleic acid molecule containing a DFHBI-binding aptamer sequence is illuminated with light, the complex emits fluorescence at first, but then the DFHBI family molecule dissociates from the DFHBI-binding aptamer sequence due to structural change and fluorescence emission stops. However, when illumination is interrupted, the structure changes again, the DFHBI family molecule and the fluorogenic nucleic acid molecule are recombined, and fluorescence reappears (Non-Patent Document 17). By utilizing this photo-dependent structural change, it is possible to improve the S/N ratio (signal-to-noise ratio) of fluorescence signals detected from the fluorogenic nucleic acid molecule that binds to the DFHBI family molecule.

Specifically, from a value of brightness (value of intensity) of a fluorescence signal obtained in a state where the DFHBI family molecule bound to a fluorogenic nucleic acid molecule to be paired emits fluorescence (on state), a value of brightness of a fluorescence signal obtained in a state where the DFHBI family molecule having dissociated from the fluorogenic nucleic acid molecule does not emit fluorescence (off state) is subtracted, and the result of subtraction is detected as a fluorescence signal emitted from the DFHBI family molecule bound to the fluorogenic nucleic acid molecule to be paired. In the fluorescence signals obtained from the DFHBI family molecule in the off state, signals (noise) such as background fluorescence and autofluorescence emitted from substances other than the DFHBI family molecule appear. Therefore, subtracting the value of brightness in the off state from the value of brightness in the on state increases the S/N ratio of the fluorescence signals emitted from the DFHBI family molecule.

The fluorescence signal of the on state and the fluorescence signal of off state can be obtained, for example, by continuously illuminating the DFHBI family molecule bound to the fluorogenic nucleic acid molecule to be paired with excitation light for the fluorescent molecule (at a wavelength capable of generating fluorescence by exciting the fluorescent molecule) for at least a time period long enough for inducing structural change causing a transition to the off state from the on state. The fluorescence signal at an illumination start point of continuous illumination with excitation light corresponds to a fluorescence signal of on state, and the fluorescence signal at the illumination end point corresponds to a fluorescence signal of the off state. The time of continuous illumination with excitation light can be appropriately set depending on the type of DFHBI family molecule, which can be 10 to 30 ms for example. That is, after the DFHBI family molecule is bonded to the fluorogenic nucleic acid molecule containing the DFHBI-binding aptamer sequence, the fluorogenic nucleic acid molecule is continuously illuminated for a certain period of time with excitation light for the DFHBI family molecule, a value of brightness of the fluorescence signal at the illumination end point is subtracted from a value of brightness of the fluorescence signal at the illumination start point, and a value of brightness obtained by the subtraction is detected as a fluorescence signal emitted from the DFHBI family molecule bound to the fluorogenic nucleic acid molecule.

In a case where illumination is interrupted, the DFHBI family molecule experiences again structural change and is recombined with the DFHBI-binding aptamer sequence in the fluorogenic nucleic acid molecule, and fluorescence reappears accordingly. Therefore, for example, by performing illumination with excitation light for enough time to obtain a fluorescence signal of the on state and a fluorescence signal of the off state and then interrupting illumination for a certain period of time, the DFHBI family molecule experiences again structural change and is recombined with the DFHBI-binding aptamer sequence in the fluorogenic nucleic acid molecule. The excitation light illumination interruption time can be appropriately set depending on the type of DFHBI family molecule, which can be 5 to 20 sec for example.

By interrupting the illumination with excitation light by means of shading and then resuming the illumination with excitation light in a state where the DFHBI family molecule has been recombined with the DFHBI-binding aptamer sequence in the fluorogenic nucleic acid molecule, it is possible to obtain again fluorescence signals of the on state and off state from the same sample. By repeating cycles each consisting of continuous illumination with excitation light and the subsequent non-illumination state, it is possible to obtain fluorescence signals of the on state and off state from the same sample plural times. By averaging the fluorescence signals, it is possible to further improve the accuracy in detecting the fluorescence signal emitted from the DFHBI family molecule.

Specifically, the fluorogenic nucleic acid molecule to be paired that has bound to the fluorescent molecule of the DFHBI family is repeatedly illuminated in multiple illumination cycles each consisting of continuous illumination with the excitation light for a certain period of time followed by interruption of illumination for a certain period of time. For each illumination cycle, a fluorescence signal at the illumination start point of the continuous illumination and a fluorescence signal at the illumination end point are detected. By averaging the values of brightness of the fluorescence signals at the continuous illumination start point detected for all illumination cycles, it is possible to improve accuracy in detecting the fluorescence signal at the illumination start point, that is, the fluorescence signal of the on state. Likewise, by averaging the values of brightness of the fluorescence signals at the illumination end point of the continuous illumination detected for all illumination cycles, it is possible to improve accuracy in detecting the fluorescence signal at the illumination end point, that is, the fluorescence signal of the off state. The averaged values of brightness of the fluorescence signals at the illumination end point are subtracted from the averaged values of brightness of the fluorescence signals at the illumination start point, and the obtained value of brightness is detected as the fluorescence signal of the DFHBI family molecule bound to the fluorogenic nucleic acid molecule.

Method of Screening Substance Inhibiting Binding of Fluorescent Molecule to Fluorogenic Nucleic Acid Molecule to be Paired By using the fluorescence signal produced as a result of binding of a fluorescent molecule to the fluorogenic nucleic acid molecule to be paired as an index, it is possible to screen an inhibitor that inhibits the binding of the two molecules. A candidate substance of the inhibitor is incorporated into a reaction system in which the fluorescent molecule and the fluorogenic nucleic acid molecule to be paired coexist, and fluorescence signals emitted from the fluorescent molecule are measured and compared with fluorescence signals emitted from the fluorescent molecule bound to the fluorogenic nucleic acid molecule in the absence of the candidate substance. In a case where the value of brightness of the fluorescence signal emitted from the fluorescent molecule in the presence of the candidate substance is lower than the value of brightness of the fluorescence signal in the absence of the candidate substance, the candidate substance is selected as an inhibitor that inhibits the binding of the fluorescent molecule to the fluorogenic nucleic acid molecule to be paired.

For example, in a case where a protein is a candidate substance, a gene encoding the candidate substance is introduced into a cell expressing the fluorogenic nucleic acid molecule which is single-stranded RNA, so that the cell expresses the gene. A fluorescent molecule is incorporated into the cell expressing the candidate substance gene and a cell that does not express such a gene, and fluorescence signals are detected. In a case where the fluorescence signal produced from the cell expressing the candidate substance gene is weaker than the fluorescence signal produced from the cell that does not express the candidate substance gene, the candidate substance is selected as an inhibitor that inhibits the binding of the fluorescent molecule to the fluorogenic nucleic acid molecule to be paired. The fluorescence signal of each cell can be obtained from the fluorescence image acquired by illuminating the cell with excitation light.

For example, the DFHBI-binding aptamer sequence forms a stem-loop structure flanked by G-quadruplex structures. In a case where a DFHBI family molecule is flanked by the G-quadruplex structures, fluorescence is emitted (Non-Patent Document 18). In a case where the G-quadruplex structures are unfolded, the aptamer sequence cannot bind to a DFHBI family molecule, and fluorescence disappears. Although eukaryotic cells are considered to contain an enzyme (G4 resolvase) that unfolds the G-quadruplex structures, the enzyme has not yet been identified (Non-Patent Document 19).

Therefore, a gene encoding a candidate protein of G4 resolvase is further introduced into a recombinant cell expressing a fluorogenic nucleic acid molecule containing a DFHBI-binding aptamer sequence so that the cell expresses the gene. A DFHBI family molecule is introduced into the cell co-expressing the fluorogenic nucleic acid molecule containing the DFHBI-binding aptamer sequence and the candidate protein gene, and fluorescence signals are measured. In a case where the obtained value of brightness is lower than the value of brightness of a fluorescence signal obtained by introducing a DFHBI family molecule into a cell expressing only the fluorogenic nucleic acid molecule containing a DFHBI-binding aptamer sequence, the candidate protein is selected as a substance having G4 resolvase activity. The DFHBI family molecule and the fluorogenic nucleic acid molecule containing a DFHBI-binding aptamer sequence can be applied to the comprehensive genetic identification of G4 resolvase.

EXAMPLES

Next, the present invention will be more specifically described with reference to Examples and the like, but the present invention is not limited to these examples.

Plasmid

The plasmids used in the following experiments were prepared as below.

3×NLS (LVPKKKRKVVPKKKRKVVPKKKRKVFEGPDPPV: SEQ ID NO: 21) and the coding sequence of iRFP713 (abbreviated to iRFP hereinafter, a kind gift from Michiyuki Matsuda, Non-Patent Document 11) were fused and subcloned into the NheI/NotI sites of pEGFP-N1 (manufactured by Clontech), thereby obtaining pNLS-iRFP. For screening the candidate (candidate RNA) of fluorogenic RNA to be paired with a DFHBI family molecule, F30-2×dBroccoli was PCR-amplified from pAV5S-F30-2×dBroccoli (#66845, manufactured by Addgene). Other RNAs were constructed from synthetic oligonucleotide fragments. By using In-Fusion (manufactured by Clontech), these oligonucleotide fragments were subcloned into the NotI site of pNLS-iRFP. Primers for In-Fusion were designed so that only the 3' side of the NotI site would be recovered. Tandem repeats of the RNA fragments were constructed by repeatedly inserting the single fragment into the NotI site. After screening, candidate RNA "Romanesco" (RNA #14) found to have the highest fluorogenic effect was PCR-amplified and subcloned into the multicloning site of pBluescript II SK (+) (manufactured by Stratagene).

For the doxycycline (DOX)-inducible Romanesco expression, the TRE3G promoter derived from pAdenoX-Tet3G (manufactured by Clontech), the NLS-iRFP coding sequence, and the Romanesco sequence were fused and subcloned into pT2-MCS-PGK-Puro vector (Non-Patent Document 12) containing recognition sequences for Tol2, cHS4 insulators, and puromycin resistance gene expression cassette, thereby obtaining pT2-TRE3G-NLS-iRFP-Romanesco.

Cell Culture and Transfection

In the following experiments, unless otherwise specified, cell culture and transfection were performed as below.

HEK293T, MCF-7, and U2OS cells were cultured in DMEM (manufactured by FUJIFILM Wako Pure Chemical Corporation) supplemented with 10% FBS, 1 mM sodium pyruvate, and 1% penicillin/streptomycin at 37° C. under 5% CO2. The cells were transfected using a transfection reagent (trade name: "X-tremeGENE HP DNA", manufactured by Hoffmann-La Roche Ltd.) according to the manufacturer's instructions. For microscopic analysis, the cells were replated onto glass-bottom dishes (manufactured by MatTek Corporation) coated with Matrigel (manufactured by BD biosciences) before imaging.

Reference Example 1

F30-2×dBroccoli (plasmid obtained by inserting the base sequence of dBroccoli into 2 loop structures in F30 scaffold sequence, SEQ ID NO: 22) has been reported to have the highest fluorescence intensity among Broccoli variants. Therefore, in order to investigate whether F30-2×dBroccoli can visualize RNA polymerase II (Pol II)-dependent mRNA in human cells, F30-2×dBroccoli that emits green fluorescence downstream side of RNA polymerase II-dependent CMV promoter in the presence of DFHBI-1T and NLS-iRFP (nuclear-localized near-infrared fluorescent protein iRFP) were co-expressed in HEK293T cells. Specifically, HEK293T cells were transfected with a plasmid vector (pNLS-iRFP-#0) prepared by incorporating F30-2×dBroccoli into the 3' untranslated region of pNLS-iRFP to express NLS-iRFP, and cultured in a culture medium supplemented with DFHBI-1T.

As a result, NLS-iRFP-positive cells transfected with pNLS-iRFP-#0 showed almost no detectable green fluorescence. That is, the existing fluorescent molecule-binding aptamer could not visualize mRNA in human cells.

Next, HEK293T cells were transfected with a plasmid vector prepared by incorporating a sequence consisting of tandemly and directly linked F30-2×dBroccoli into the 3' untranslated region of pNLS-iRFP, and cultured in a medium supplemented with DFHBI-1T in the same manner as described above. As a result, it was confirmed that the larger the number of repeats of F30-2×dBroccoli is, the larger the number of cells tends to be in which significant green fluorescence is observed. This result suggests that by optimizing the fluorescent molecule-binding aptamer, the fluorescence intensity of DFHBI family molecules could be sufficiently improved so that subcellular RNA can be visualized.

Example 1

Fluorogenic RNA to be paired with DFHBI family molecules, that is, fluorogenic RNA capable of improving fluorescence intensity generated by binding to DFHBI family molecules, was screened.

As shown in FIG. 1, all known fluorescent molecule-binding aptamers such as Spinach and Broccoli have similar sequences, and consist of a terminal stem ("Terminal stem" in the figure), G-quadruplex, stem-loop, and a connector. These segments are determined by the crystal structure of Spinach and by base sequence alignment against other fluorescent molecule-binding aptamers.

For the terminal stem, it has been suggested that an A:G purine-purine mismatch and a C-G Watson-Crick base pair in the duplex-to-quadruplex transition region, which is contained in Spinach variants, strongly affect the brightness of the aptamer in a cellular environment (Non-Patent Document 9). Therefore, GAGAC-GGCUC was used as a terminal stem sequence.

In a case where a G-quadruplex was focused on, substantially no change was found in the sequence thereof, except that Spinach and dBroccoli contain the characteristic single nucleotide substitution C of U at the third position in the second half of the G-quadruplex. Therefore, the inventors of the present invention decided to employ the sequences derived from Broccoli and dBroccoli (GGUCGGGUCC-GUCGAGUAGAGUGUG) or the sequence derived from Broccoli3 (GGUCGGGUCC-GUUGAGUAGAGUGUG) for the G-quadruplex.

For the stem-loop, simply a stem-loop derived from Broccoli was used for Broccoli, and a stem-loop of dBroccoli G-quadruplex and a Broccoli3 stem-loop were used for the Broccoli3 G-quadruplex. Furthermore, a chimera of a Broccoli3 G-quadruplex and an iSpinach stem-loop containing a 6 bp (base pair length) stem and a 4 nt (base length) loop was used.

F30 scaffold has been reported to enhance the fluorogenicity of fluorescent molecule-binding aptamers for the DFHBI family in mammalian cells (Non-Patent Document 10). Therefore, for comparison, candidate RNAs with or without an F30 scaffold sequence were constructed.

Because tandemly linking F30-2×dBroccoli could improve the generated fluorescence intensity (Reference Example 1), fluorogenic RNA was constructed by tandemly linking the fluorescent molecule-binding aptamer sequences incorporated into the scaffold sequence (F30 scaffold sequence) via a linker sequence, and the number of tandem repeats of fluorescent molecule-binding aptamer sequences incorporated into the scaffold sequence was changed in an attempt to optimize the fluorogenic RNA. The number of tandem repeats was set to be 6 or less so as to make the fluorogenic RNA as small as possible and to avoid recombination events. "Romanesco" (RNA #14) designed and synthesized as will be described later that contained 6 repeats did not cause recombination during the study both in bacterial cells and mammalian cells (data is not shown).

Linker sequences with lengths of 30, 44, or 66 nt were inserted between the fluorescent molecule-binding aptamer sequences incorporated into the scaffold sequence. The linker sequences were optimized using RNA 3-dimensional structure prediction software "mFold" so that they would not disturb the secondary structure of the F30 scaffold and the fluorescent molecule-binding aptamer.

Specifically, the linker sequences were designed as follows. First, candidate linker sequences were designed in which a random sequence consisting of 4 types of RNAs, AUGC, was adopted as a sequence of a region excluding 6 bases corresponding to the restriction enzyme site. The random sequence consisting of 4 types of RNAs, AUGC, was designed using the RANDBETWEEN function of the spreadsheet software "Microsoft Excel".

Next, for each of the designed candidate linker sequences, an RNA sequence for evaluation consisting of the F30-2× dBroccoli sequence with the candidate linker sequences linked to upstream and downstream side thereof (candidate linker sequence-F30-2×dBroccoli sequence-candidate linker sequence) was designed, and the 3-dimensional structure thereof was predicted. To predict the 3-dimensional structure, the inventors of the present invention had access to the RNA 3-dimensional structure prediction software "mFold" ([on line] http://unafold.rna.albany.edunq=mfold/RNA-Folding-Form), entered the obtained RNA sequence for evaluation, set "Enter the maximum distance between paired bases if you wish" to 150 while leaving other parameters at default values, and clicked "Fold RNA" to execute the software. "Enter the maximum distance between paired bases if you wish" was set to 150 so as to prevent base pairing between linker sequences.

For the 3-dimensional structure predicted by "mFold", whether the 3-dimensional structure of the F30-2×dBroccoli sequence is disrupted by the candidate linker sequence or whether the candidate linker sequence is a flexible region were confirmed. Specifically, whether or not the 3-dimensional structure of the F30-2×dBroccoli sequence portion is identical to the 3-dimensional structure predicted only from the F30-2×dBroccoli sequence was confirmed. In a case where the sequences are confirmed to have different 3-dimensional structures, the candidate linker sequence is predicted to disrupt the 3-dimensional structure of the F30-2×dBroccoli sequence. Furthermore, in a case where the candidate linker sequence portion is not predicted to have a specific 3-dimensional structure, the candidate linker sequence is predicted to be a flexible region.

Among the candidate linker sequences, a candidate linker sequence for which "mFold" predicted that the RNA sequence for evaluation would have a 3-dimensional structure, in which the F30-2×dBroccoli sequence portion has a 3-dimensional structure identical to a 3-dimensional structure predicted from only the F30-2×dBroccoli sequence and the candidate linker sequence portion is not predicted to have a specific 3-dimensional structure, was selected as a linker sequence. Finally, as linker sequences, those listed in Table 3 were selected. The following candidate RNAs were synthesized using linker sequences of SEQ ID NOS: 18, 19, and 20 having the lowest free energy (ΔG) among sequences of different base lengths. For example, regarding those listed in Table 4, it was predicted that the candidate linker sequence portion would have a 3-dimensional structure or a 3-dimensional structure of the F30-2×dBroccoli sequence portion would change due to the influence on the linker sequence portion. Therefore, those listed in Table 3 were evaluated as being preferable as linker sequences.

TABLE 4

| | Sequence | SEQ ID NO |
|---|---|---|
| 30 nt linker | GGAUGACGAGGCGGCCUGGUUAAAAGGUAG | 38 |
| | CGAUCUAGGAGCGGCCAGUUACGCGGUGGA | 39 |
| | CUCACAACAAGCGGCCGUAACUGCCUUUGU | 40 |
| 44 nt linker | GAUCGACUGAGGAUAUGUUGCGGCCGUUGGACCUGGAGAGUCCU | 41 |
| | CUUAUAGUAGUCCAUGGUCGCGGCCUGUUUAAACGGCUAGUCUA | 42 |
| | CGUAGUAUACGCGCGUGUGGCGGCCCAUCGAUCUUCCCGUGCUU | 43 |
| 66 nt linker | UAUAUUCGGCUAAUCAACAUCCCAACACGCGGCCGUCGACCGUGACAGAGAACGCCUGAAUAGUAA | 44 |
| | UCAUCUUAGCGUGCACACACUGGUUCCAGCGGCCGUGAACGCCUCGUGCGCAUUUGAGUGUGCUUG | 45 |
| | ACUCUUUUGAACGCCCGAUAGUGGCGUGGCGGCCCUUCCGGCAAUAUGUACCUGCAGAACUAGUAA | 46 |

First, 17 candidate RNAs (RNA #1 to #17) were designed. RNA #1 is RNA consisting only of broccoli (SEQ ID NO: 12). RNA #2 is RNA consisting of 1 fluorescent molecule-binding aptamer sequence obtained by inserting 2 Broccoli into the F30 scaffold sequence. RNA #3 to RNA #5 are RNAs in which 2, 4, or 6 fluorescent molecule-binding aptamer sequences each obtained by inserting 2 Broccoli into the F30 scaffold sequence are linked via 44 nt linker sequence (SEQ ID NO: 19). RNA #6 is RNA in which 12 RNAs (SEQ ID NO: 12) consisting only of Broccoli are directly linked in tandem without a linker sequence. RNA #7 to RNA #9 are RNAs in which 2, 4, or 6 fluorescent molecule-binding aptamer sequences each obtained by inserting 2 dBroccoli (SEQ ID NO: 14) into the F30 scaffold sequence are linked via a 44 nt linker sequence (SEQ ID NO: 19). RNA #10 is RNA consisting only of broccoli3 (SEQ ID NO: 13). RNA #11 is RNA consisting of 1 fluorescent molecule-binding aptamer sequence obtained by inserting 2 Broccoli3 into the F30 scaffold sequence. RNA #12 to RNA #14 are RNAs in which 2, 4, or 6 fluorescent molecule-binding aptamer sequences each obtained by inserting 2 Broccoli3 into the F30 scaffold sequence are linked via 44 nt linker sequence (SEQ ID NO: 19). RNA #15 is RNA obtained by substituting the stem-loop region of Broccoli3 in RNA #14 with the base sequence represented by SEQ ID NO: 6. RNA #16 is RNA in which 12 RNAs (SEQ ID NO: 13) consisting only of Broccoli3 are directly linked in tandem without a linker sequence. RNA #17 is RNA obtained by substituting the stem-loop region of Broccoli3 in RNA #16 with the base sequence represented by SEQ ID NO: 6.

The designed 17 candidate RNAs (RNA #1 to #17) were incorporated into the 3' untranslated region of pNLS-iRFP in the same manner as in pNLS-iRFP-#0, thereby preparing pNLS-iRFP-#1 to #17. HEK293T cells were transfected with the prepared plasmids so that the cells expressed the plasmids, and the fluorogenicity thereof was evaluated by measuring green fluorescence intensity of NLS-iRFP-positive cells in the presence of DFHBI-1T by using a conventional laser scanning confocal microscope.

Specifically, HEK293T cells transfected with the plasmid prepared in the same manner as in Reference Example 1 were plated onto glass-bottom dishes and cultured. Twenty-four hours after transfection, the cells were imaged using a confocal microscope (trade name: "A1R", manufactured by Nikon Corporation) having an oil immersion objective lens (trade name: "Plan Fluor 40×/1.30" manufactured by Nikon Corporation). For the cells, a 488 nm laser beam (Melles Griot., 0.5 μW) was used to excite the candidate fluorogenic RNA, and a 640 nm laser beam (Coherent, 3 μW) was used to excite NLS-iRFP. Scanning with the confocal microscope was bidirectional at the highest possible rate with a 2× magnification, and the pinhole was closed to 100 For each field-of-view, a stack of 7 images separated by 1 μm was acquired as z sections. During imaging, DFHBI-1T (manufactured by Tocris) was added to L-15 medium (manufactured by Thermo Fisher Scientific) to a final concentration of 20 μM. The experiment was carried out at room temperature.

The acquired images were analyzed using image analysis software (trade name: "Fiji" from National Institutes of Health). The images were first converted into 32-bit floating-point images. For each field-of-view, cellular fluorescence intensities elicited by a 488 nm laser and a 640 nm laser were calculated as follows. First, the average projections of the 488 nm channel and the 640 nm channel were obtained for all the z sections. Next, the averaged 640 nm channel image mainly consisting of NLS-iRFP signal was converted into a binary image by automatic thresholding using Otsu's method, and the functions performed by the Fiji software ("Fill Holes", "Watershed", and "Analyze Particles") were used to obtain regions of interest (ROI). Cellular ROIs were defined by enlarging the nuclear ROIs by 10 pixels (1 pixel=311 nm). Finally, the average values of the nuclear ROIs were measured to obtain fluorescence intensity for the 640 nm channel, and the average values of the cellular ROIs were measured to obtain fluorescence intensity for the 488 nm channel. Fluorescence intensities of the neighboring untransfected cells were also measured for each channel, and the average values thereof were subtracted as background. As a result of the above processing, the values of the fluorescence intensity generated from DFHBI-1T by the candidate RNA and the fluorescence intensity of NLS-iRFP were obtained for each cell. Hereinafter, "fluorescence generated from a DFHBI family fluorescent molecule by fluorogenic RNA" will be referred to as "fluorescence of fluorogenic RNA" in some cases.

Figure 2:
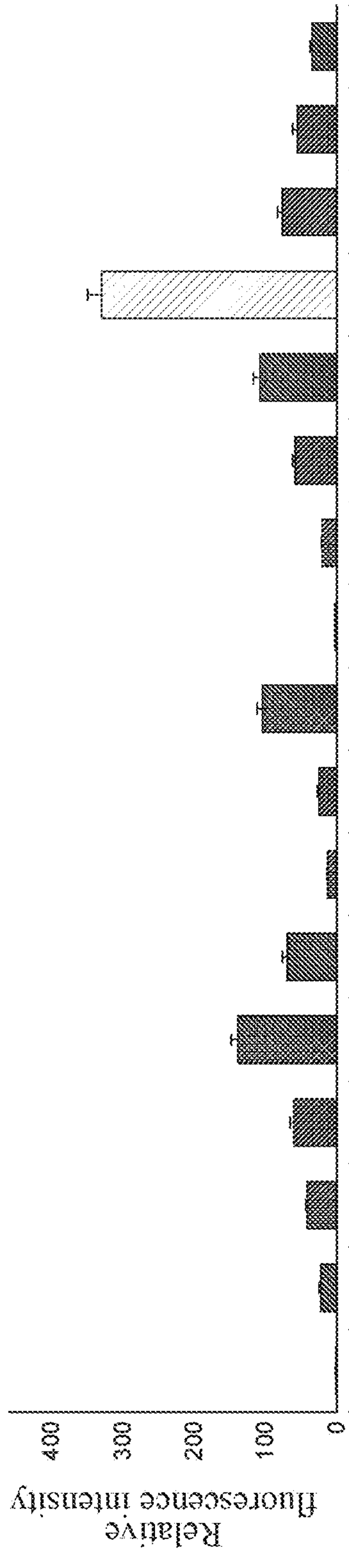
FIG. 2 is a diagram showing relative fluorescence intensity of cells expressing candidate RNAs (RNA #1 to #17) in Example 1, the relative fluorescence intensity obtained by dividing DFHBI-1T fluorescence intensity by NLS-iRFP fluorescence intensity to obtain normalized fluorescence intensity and further dividing the normalized fluorescence intensity by the average normalized fluorescence intensity of cells expressing RNA #1 (Spinach).

FIG. 2 is a diagram showing relative fluorescence intensity of cells expressing candidate RNAs (RNA #1 to #17), and the relative fluorescence intensity obtained by dividing the fluorescence intensity of candidate RNAs by NLS-iRFP fluorescence intensity to obtain normalized fluorescence intensity and further dividing the normalized fluorescence intensity by the average normalized fluorescence intensity of cells expressing RNA #1 (Spinach). The detection limit of DFHBI-1T fluorescence in cells expressing candidate RNA was determined by calculating the average+3 SD of the fluorescence intensity of the cells that do not express the candidate RNA. This was performed only on cells expressing NLS-iRFP. In the diagram, error bars represent s.e.m. The number n of cells expressing RNA #1 to #17 are 55, 310, 255, 217, 360, 316, 299, 212, 271, 282, 216, 401, 343, 229, 217, 150, and 244, respectively.

As shown in FIG. 2, all of the candidate RNAs (RNA #2 to #9 and #11 to #17) having fluorescent molecule-binding aptamer sequences tandemly linked via a linker sequence exhibited higher fluorogenicity, compared to the conventional fluorescent molecule-binding aptamer having only one fluorescent molecule-binding aptamer sequence (RNA #1 and #10).

As is evident from the cells expressing RNA #1 to #5, the cells expressing RNA #7 to #9, and the cells expressing RNA #10 to #14, the larger the number of fluorescent molecule-binding aptamer sequences tandemly linked, the brighter the fluorescence generated from the fluorescent molecule to be paired. In addition, compared to the candidate RNA having Broccoli or dBroccoli as a fluorescent molecule-binding aptamer sequence, the candidate RNA having Broccoli3 as a fluorescent molecule-binding aptamer sequence had a higher fluorogenic effect. Furthermore, as is evident from the cells expressing RNA #5 and #6 and the cells expressing RNA #14 and #16, the scaffold sequence is essential for higher fluorogenicity. As a result of comparing the cells expressing RNA #14 and #15, it was found that converting the 5 bp stem structure of the stem-loop structure in the fluorescent molecule-binding aptamer sequence into a 6 bp stem structure significantly deteriorates fluorogenicity. The cells expressing RNA #14 showed the brightest fluorescence among the cells expressing other candidate RNAs, reaching 300-fold or higher brightness compared to the cells expressing RNA #1.

Figure 3:
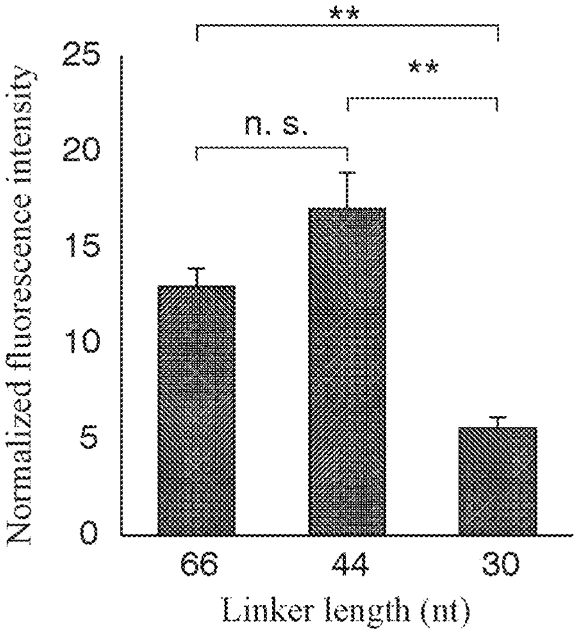
FIG. 3 is a diagram showing relative fluorescence intensity of cells caused to express candidate RNAs (RNA #14, #18, and #19) in Example 1, the relative fluorescence intensity obtained by dividing DFHBI-1T fluorescence intensity by NLS-iRFP fluorescence intensity to obtain normalized fluorescence intensity and further dividing the normalized fluorescence intensity by the average normalized fluorescence intensity of cells caused to express RNA #1 (Spinach).

For RNA #14, in order to investigate the influence of linker sequence length on the fluorogenicity, the 44 nt linker sequence (SEQ ID NO: 19) in RNA #14 was changed to a 30 nt linker sequence (SEQ ID NO: 18) to design RNA #18 and changed to a 66 nt linker sequence (SEQ ID NO: 20) to design RNA #19, and the fluorogenicity thereof was examined in the same manner as described above. FIG. 3 shows the results. In FIG. 3, error bars represent s.e.m. (n=94, 68, or 57). The Kruskal-Wallis test ($p<0.001$) was performed, followed by the Steel-Dwass test (**: $p<0.01$, n.s.: $p>0.05$).

As a result, just as RNA #14, both the RNA #18 and RNA #19 exhibited higher fluorogenicity compared to the conventional RNA #1. RNA #14 had the best fluorogenicity among the three candidate RNAs.

RNA #14 capable of visualizing mRNA in living mammalian cells was named "Romanesco" and used in the following experiments.

Example 2

Romanesco prepared in Example 1 was confirmed to allow quantitative measurement of mRNA in living cells.

DFHBI family molecules generate sufficient fluorescence intensity only after binding to fluorescent molecule-binding aptamers to be paired, such as Romanesco. Therefore, the total fluorescence intensity of cells derived from the DFHBI family directly reflects the expression level of mRNA containing Romanesco. That is, tagging mRNA of a target gene with Romanesco makes it possible to quantitatively evaluate the expression level of the target gene based on the fluorescence intensity of the DFHBI family.

Romanesco-tagged mRNA of a target gene was expressed under the control of a doxycycline (DOX)-inducible promoter, and the changes in the fluorescence signal of Romanesco of the cell and the mRNA synthesis of the target gene were monitored together in the presence of the DFHBI family.

Imaging of Dynamics of mRNA Synthesis and Degradation

HEK293T cells were transfected with pT2-TRE3G-NLS-iRFP-Romanesco to obtain cells having a reporter gene expressing NLS-iRFP and Romanesco, and these cells were used as reporter cells.

For time-lapse imaging of Romanesco during transcriptional activation, the reporter cells were cultured in DMEM (without phenol red, manufactured by FUJIFILM Wako Pure Chemical Corporation) containing 4 mM L-glutamine, 10% FBS, 1 mM sodium pyruvate, 1% penicillin/streptomycin, and 20 μM DFHBI-1T under the control of DOX-inducible promoter. The cells were imaged with a confocal microscope MR using an oil immersion objective lens Plan Fluor 40×/1.30 at 37° C. under 5% $CO_2$. DOX (manufactured by Clontech) with a final concentration of 1 μg/mL was added to the medium to induce transcription, a 488 nm laser beam (0.5 μW) was used to excite Romanesco, and a 640 nm laser beam (3 μW) was used to excite NLS-iRFP. Scanning was bidirectional at the highest possible rate with a 2× magnification, and the pinhole was closed to 100 μm. For each field-of-view, a stack of 13 images separated by 1 μm was acquired as z sections with 10-min intervals for 8 hours.

For time-lapse imaging of Romanesco during transcriptional inactivation, the reporter cells were incubated in the presence of DOX at 1 μg/ml for 12 hours, subjected to imaging as described above, and then ActD at a final concentration of 5 μg/ml was added thereto to inhibit transcription.

The acquired images were processed, and the fluorescence intensity of each cell was measured in the same manner as in Example 1. The obtained fluorescence intensities of Romanesco and NLS-iRFP were normalized so that the average fluorescence intensity at 8 hr after DOX addition was 1 and the average fluorescence intensity at 0 hr after ActD addition was 1.

Determination of Romanesco-Labeled mRNA Expression Level by RT-qPCR

To analyze the dynamics of Romanesco-labeled mRNA synthesis in reporter cells during transcriptional activation, HEK293T cells stably expressing the DOX-inducible reporter gene were plated onto a 24-well plate, treated with DOX at a final concentration of 1 μg/mL, and recovered from each well at 0, 0.5, 1, 1.5, 2, 3, 4, 5, 6 and 8 hr after DOX addition. For analyzing the mRNA degradation dynamics during transcriptional inactivation, HEK293 cells stably expressing the DOX-inducible reporter gene were plated onto a 24-well plate, treated with DOX at a final concentration of 1 μg/mL for 12 hr and then with ActD at a final concentration of 5 μg/mL, and recovered from each well at 0, 1, 2, 3, 4, 5 and 6 hr after ActD addition.

The cells were then lysed, and RNA was purified with FastGene RNA Premium Kit (manufactured by NIPPON Genetics). The obtained RNA was reverse transcribed and quantified by real-time PCR with CFX96 system (manufactured by Bio-Rad Laboratories, Inc.) using One Step SYBR PrimeScript PLUS RT-PCR Kit (manufactured by Takara Bio Inc.). The reverse transcription and PCR reactions were performed under the following conditions: 42° C. for 5 min, 95° C. for 10 sec followed by 50 cycles of 10 sec at 95° C. and 30 sec at 60° C.

The specificity of the amplicon was investigated by performing dissociation curve analysis according to the manufacturer's protocol. For analyzing the expression level of reporter mRNA, a PCR primer set that amplifies the coding sequence of NLS-iRFP (forward primer: 5'-CCAATCCACATTCCAGGAGCTATC-3' (SEQ ID NO: 23), reverse primer: 5'-CTTTCGCATTGTGAAGCCGAC-3' (SEQ ID NO: 24)) was used, because Romanesco has multiple repeats within the Romanesco sequence. For DOX-treated samples, PGK1 gene was selected as internal control, because the expression level of PGK1 is not affected by DOX treatment and the amplification efficiency of the primer set for PGK1 amplification (forward primer: 5'-TGGACGTTAAAGGGAAGCGGG-3' (SEQ ID NO: 25), reverse primer: 5'-GGCTCATAAGGACTACCGACTTGGC-3' (SEQ ID NO: 26)) is comparable to the amplification efficiency of the primer set for NLS-iRFP (data is not shown). For ActD-treated samples, 18S ribosomal RNA was selected as internal control, because the expression level of 18S ribosomal RNA is not affected by ActD treatment and the amplification efficiency of the primer set for 18S ribosomal RNA amplification (forward primer: 5'-CGGCTACCACATCCAAGGAAG-3' (SEQ ID NO: 27), reverse primer: 5'-TTTTTCGTCACTACCTCCCCG-3' (SEQ ID NO: 28) is comparable to the amplification efficiency of the primer set for NLS-iRFP (data is not shown).

The experiment was performed in 3 biological replicates. For each biological replicate, RT-qPCR analyses were performed in triplicate for each primer set. The relative expression levels of the reporter mRNA were determined using the ΔΔCq method. The obtained values were further normalized so that the average expression level at 8 hr after DOX addition was 1 for DOX-treated samples and the average expression level at 0 hr after ActD addition was 1 for ActD-treated samples.

Figure 4:
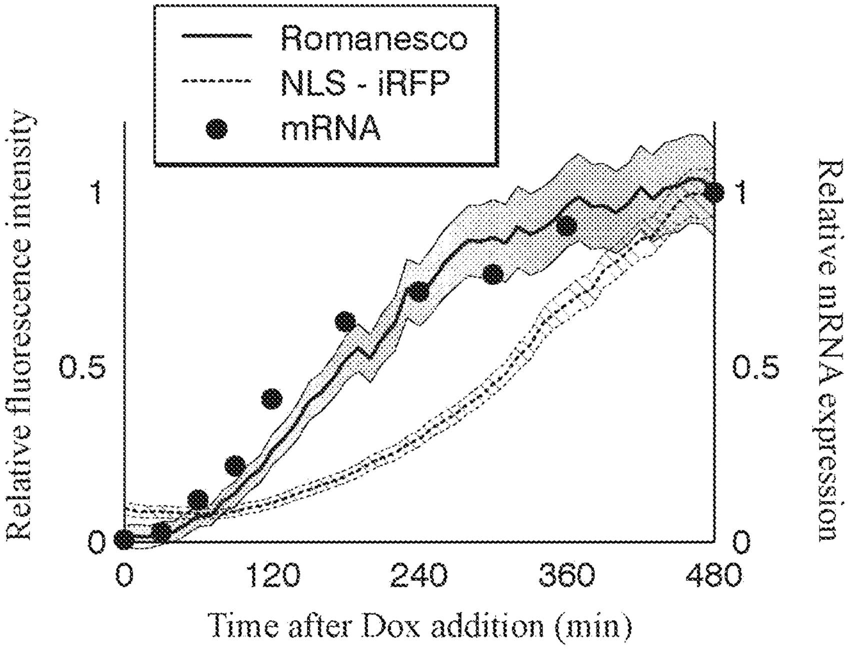
FIG. 4 is a diagram showing quantification results of fluorescence of Romanesco and NLS-iRFP and quantification results of an mRNA expression level of Romanesco-tagged NLS-iRFP after Dox treatment in Example 2.

FIG. 4 shows the quantification results of the fluorescence of Romanesco and NLS-iRFP (green and magenta, respectively) after Dox treatment, and the quantification results of the expression level of Romanesco-tagged NLS-iRFP mRNA measured by RT-qPCR (black dot). The quantified fluorescence of Romanesco and NLS-iRFP is the result of n=66 cells. RT-qPCR was performed in 3 biological replicates. In FIG. 4, the dotted area and the shaded area represent average±s.e.m. The fluorescence dynamics of Romanesco and NLS-iRFP were compared with the dynamics of mRNA expression level. As a result, it was found that the fluorescence dynamics of Romanesco faithfully followed the dynamics of mRNA synthesis, and the fluorescence signal of Romanesco rapidly increased immediately after the addition of DOX. In contrast, the fluorescence signal of NLS-iRFP was delayed.

Figure 5:
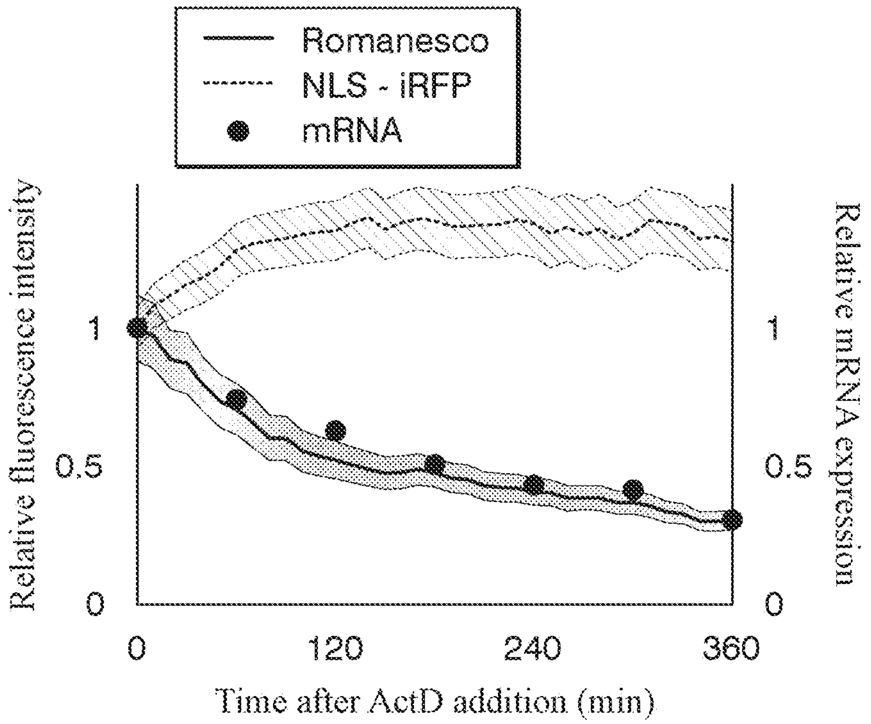
FIG. 5 is a diagram showing quantification results of fluorescence of Romanesco and NLS-iRFP and quantification results of an mRNA expression level of Romanesco-tagged NLS-iRFP after ActD treatment in Example 2.

FIG. 5 shows the quantification results of the fluorescence of Romanesco and NLS-iRFP after ActD treatment, and the quantification results of the expression level of Romanesco-tagged NLS-iRFP mRNA measured by RT-qPCR (black dot). In FIG. 5, the dotted area and the shaded area represent average±s.e.m. The quantified fluorescence of Romanesco and NLS-iRFP is the result of n=67 cells. RT-qPCR was performed in 3 biological replicates. In a case where transcription was inactivated by ActD treatment, the NLS-iRFP fluorescence signal was sustained, but the Romanesco fluorescence signal showed a steep decrease, which was consistent with the mRNA degradation dynamics. These results show that monitoring of Romanesco fluorescence makes it possible to quantitatively measure mRNA synthesis and degradation in living cells.

Single-Cell Analysis of Linearity Between mRNA Copy Number and Romanesco Signal

Figure 6:
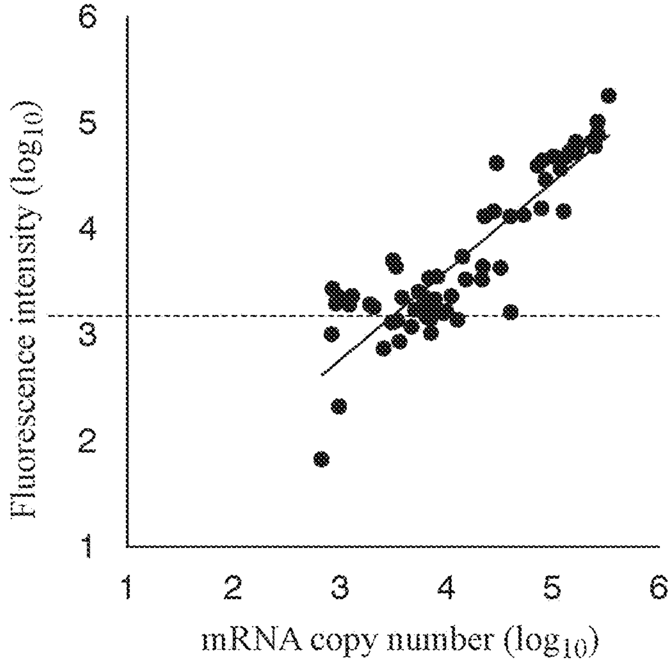
FIG. 6 is a diagram showing the results of single-cell analysis of linearity between mRNA copy number and Romanesco signal in Example 2.

Whether Romanesco signals linearly reflect the mRNA copy number for each single cell was also investigated. Specifically, cells expressing Romanesco were first imaged by conventional epifluorescence microscopy for determining Romanesco signals, and then subjected to a single-cell RT-qPCR experiment to analyze the copy number of expressed mRNA molecules for each single cell. FIG. 6 shows the results. In FIG. 6, the dashed line represents average+3 SDs of the background signal corresponding to the detection limit (n=63 cells). The solid line represents linear regression to logarithmically transformed data. As a result, a high linear correlation between mRNA copy number and Romanesco signal was confirmed in a range of $10^3$ to $3\times10^5$ molecules ($R^2$=0.87).

Time-Gated FLIM

The single-cell analysis also revealed that cells with less than $5.4\times10^3$ Romanesco molecules could not be visualized by the conventional microscope. Therefore, to see whether time-gated FLIM can more sensitively visualize Romanesco expression, cells with a low copy number of Romanesco were observed by both the conventional epifluorescence microscopy and time-gated FLIM to compare the fluorescence signals.

Figure 7:
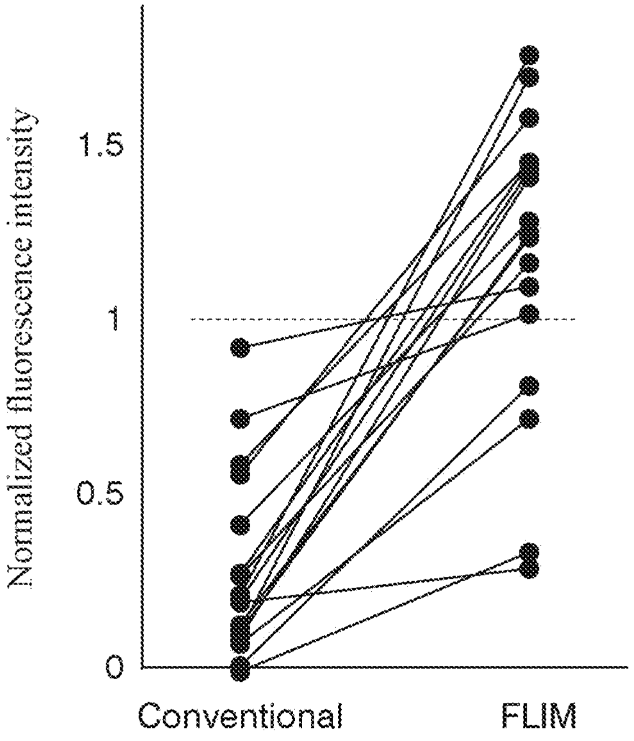
FIG. 7 is a diagram showing results of fluorescence signals obtained from cells by epifluorescence microscopy and time-gated FLIM in Example 2.

FIG. 7 shows the results of fluorescence signals obtained from cells by epifluorescence microscopy and time-gated FLIM. The fluorescence signal intensities were normalized so that the fluorescence intensity corresponding to the detection limit of each microscope (dashed line) was 1. As shown in FIG. 7, most of the cells that showed the fluorescence below the detection limit in conventional microscopy exhibited significant fluorescence in time-gated FLIM (13 out of 17 cells). That is, time-gated FLIM greatly enhanced the detection sensitivity, and cells expressing as low as $1.4\times10^3$ molecules, which is close to the mRNA levels of endogenous genes, were successfully visualized. These results clearly show that Romanesco can quantitatively determine the cellular content of specific mRNA in a wide range of expression levels, and can be used for analyzing the dynamics of transcriptional activity.

Example 3

Romanesco-expressing cells prepared in Example 2 by transfecting HEK293 cells with pT2-TRE3G-NLS-iRFP-Romanesco were cultured in the presence of Dox and DFHBI-1T, and the fluorescence signals emitted from the cells were measured by epifluorescence microscopy.

First, the Romanesco-expressing cells were cultured in DMEM (without phenol red, manufactured by FUJIFILM Wako Pure Chemical Corporation) containing 4 mM L-glutamine, 10% FBS, 1 mM sodium pyruvate, 1% penicillin/streptomycin, and 20 μM DFHBI-1T. DOX (manufactured by Clontech) with a final concentration of 1 μg/mL was added to the medium to induce transcription, the cells were intermittently illuminated with a 488 nm laser beam (0.5 μW) to excite Romanesco, and fluorescence images of the Romanesco-expressing cells were acquired with an epifluorescence confocal microscope MR. The cells were illuminated with a laser beam by a program in which a cycle of exposure for 20 ms followed by shading for 8 sec was repeated 8 times. For each field-of-view, one fluorescence image was continuously captured at 10 ms intervals during the exposure for 20 ms.

In each cycle, DFHBI-1T imaged for the first 10 ms was regarded as a fluorescence image in an on state, and DFHBI-1T imaged for the subsequent 10 ms was regarded as a fluorescence image in an off state. Eight fluorescence images of on state obtained for one field-of-view were averaged and adopted as an on-state fluorescence image of that field-of-view. Likewise, 8 fluorescence images of off state obtained for one field-of-view were averaged and adopted as an off-state fluorescence image of that field-of-view. For each field-of-view, from the values of brightness of pixels of the on-state fluorescence image, the values of brightness of the corresponding pixels of the off-state fluorescence image were subtracted, and the obtained fluorescence image was adopted as a DFHBI-1T fluorescence image of the field-of-view.

Figure 8:
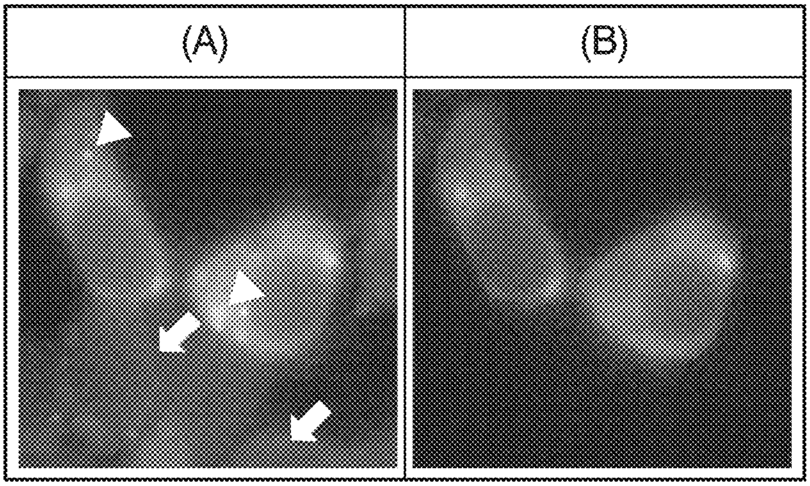
FIG. 8(A) is an on-state fluorescence image of Romanesco-expressing cells cultured in the presence of Dox and DFHBI-1T in Example 3.
FIG. 8(B) is a DFHBI-1T fluorescence image obtained by subtracting an off-state fluorescence image from the on-state fluorescence image.

FIG. 8(A) shows the on-state fluorescence image, and FIG. 8(B) shows the DFHBI-1T fluorescence image. In FIG. 8(B), the background fluorescence (arrow) derived from the Romanesco non-expressing cells and the autofluorescence (arrowhead) in the Romanesco-expressing cells in FIG. 8(A) were eliminated, resulting in imaging with a high S/N ratio.

Example 4

By using the Romanesco-expressing cells prepared in Example 2 by transfecting HEK293 cells with pT2-TRE3G-NLS-iRFP-Romanesco, screening of proteins having G4 resolvase activity was performed. Three kinds of proteins (A, B, C) were used as candidate proteins of G4 resolvase.

Specifically, the Romanesco-expressing cells were transfected with a plasmid for expressing candidate protein genes so that the cells expressed the genes, and green fluorescence intensity of NLS-iRFP-positive cells expressing the candidate proteins was measured in the presence of DFHBI-1T. The plasmid transfection and the measurement of the green fluorescence intensity of each cell were carried out in the same manner as in Example 1. As a control, green fluorescence intensity of NLS-iRFP-positive Romanesco-expressing cells that did not overexpress the candidate proteins was measured in the same manner as described above.

Figure 9:
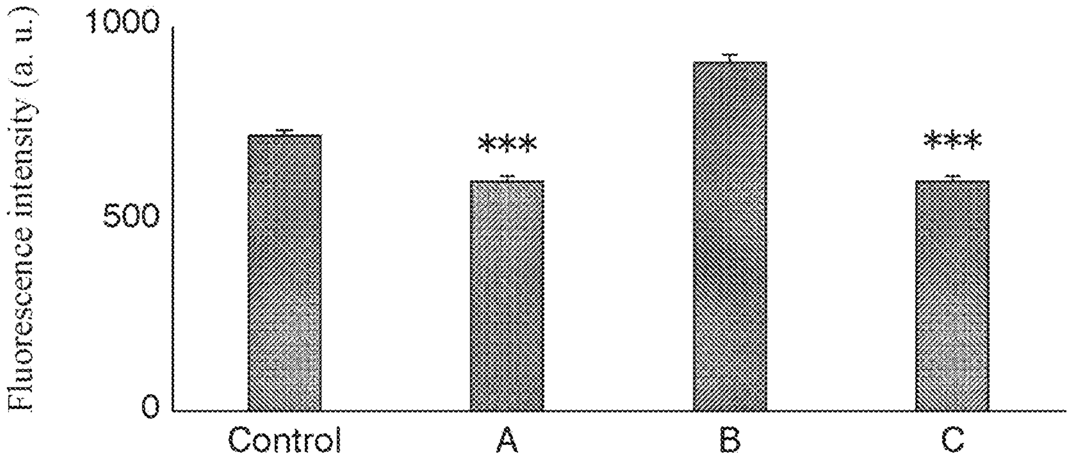
FIG. 9 is a diagram showing measurement results of green fluorescence intensity of Romanesco-expressing cells over-expressing candidate proteins A to C in Example 4.

FIG. 9 shows measurement results of green fluorescence intensity of each NLS-iRFP-positive cell. In FIG. 9, "A", "B", and "C" represent the measurement results of fluorescence intensity (A.U.) of NLS-iRFP-positive cells expressing A protein, B protein, and C protein, respectively. The cells overexpressing A protein and C protein had lower fluorescence intensities than control cells, and were selected as proteins having G4 resolvase activity.

On the other hand, the cells overexpressing B protein had a higher fluorescence intensity than control cells, and the protein was identified as a protein having an activity of improving the brightness of G4 Romanesco, that is, an activity of promoting the formation of G-quadruplex structure.

The degree of formation of the G-quadruplex structure can be measured by measuring the circular dichroism of the solution in which RNA capable of taking the G-quadruplex structure is dissolved. A protein and C protein have been reported to experience change in circular dichroism when added to a reaction solution of RNA capable of taking the G-quadruplex structure and synthesized by in vitro transcription, resulting in unfolding of the G-quadruplex structure. That is, these are proteins reported to have at least in vitro G4 resolvase activity. By the screening method in the present invention using cells, A protein and C protein were confirmed to have G4 resolvase activity even in cells.

Example 5

The expression dynamics of transcripts of a target gene were investigated using Romanesco prepared in Example 1.

Figure 10A:
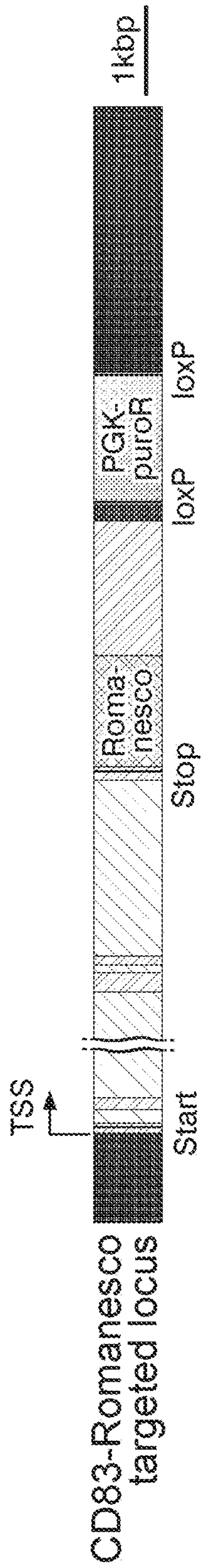
FIG. 10A is a schematic diagram of a CD83 gene locus of CD83-labeled cells in Example 5.

Specifically, first, Romanesco knock-in was introduced into 3'UTR of CD83 gene of DT40 cells, thereby preparing labeled CD83 cells. FIG. 10A is a schematic diagram of the CD83 gene locus of the labeled CD83 cells.

Figure 10B:
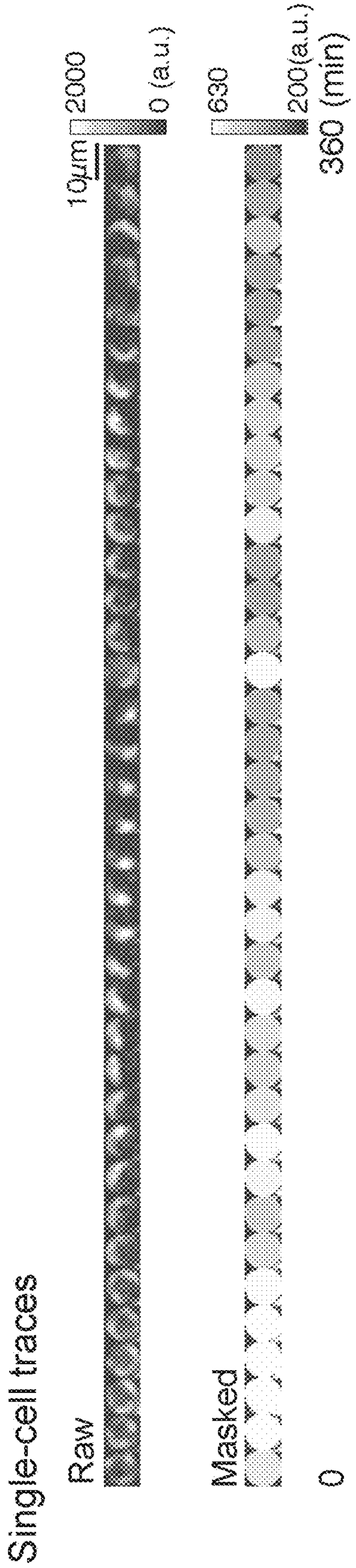
FIG. 10B is a time-lapse fluorescence image of the CD83-labeled cells stimulated with a surface antigen of CD83 in Example 5.

For stimulation, surface antigens of CD83 were added to the DFHBI-1T-containing medium in which the labeled CD83 cells were cultured, so that expression of CD83 was induced. The expression dynamics of the transcripts were observed as a change in fluorescence intensity of DFHBI-1T. The fluorescence intensity of each cell was measured by epifluorescence microscopy in the same manner as in Example 2. For each cell, fluorescence images were acquired before CD83 surface antigen stimulation (at 0 min after addition) and for 360 min after stimulation with 1 min intervals. FIG. 10B shows 37 fluorescence images acquired for a certain cell. In the figure, the top ("Raw" in the figure) shows the result of time-lapse detection of fluorescence signals of the cell, and the bottom ("Masked" in the figure) shows the result obtained by setting ROI surrounding the cell region and averaging the fluorescence intensities in ROI. Labeling of the target gene with Romanesco made it possible to continuously observe the transcriptional dynamics of the target gene at the single cell level.

What is claimed is:

1. A fluorogenic nucleic acid molecule, comprising:

a base sequence having 2 or more fluorescent molecule-binding regions linked via a linker sequence, wherein 1 or more fluorescent molecule-binding aptamer sequences are inserted into a scaffold sequence of each of the fluorescent molecule-binding regions, and the linker sequence consists of a base sequence represented by any of SEQ ID NOS: 18 to 20.

2. The fluorogenic nucleic acid molecule according to claim 1, wherein 2 or more of the fluorescent molecule-binding aptamer sequences are inserted into the scaffold sequence of each of the fluorescent molecule-binding regions.

3. The fluorogenic nucleic acid molecule according to claim 1, wherein the fluorescent molecule-binding regions each have a structure in which at least 2 loop structures in a single-stranded nucleic acid molecule forming a stem-loop structure containing 2 or more loop structures are substituted with the fluorescent molecule-binding aptamer sequences.

4. The fluorogenic nucleic acid molecule according to claim 1, wherein the fluorescent molecule-binding aptamer sequences each contain a base sequence of a single-stranded nucleic acid molecule forming a stem-loop structure flanked by G-quadruplex structures, and the stem-loop structure consists of a 4 to 6 bp stem structure and a 4 bp loop structure.

5. The fluorogenic nucleic acid molecule according to any one of claim 1, wherein the fluorescent molecule-binding aptamer sequences are Broccoli, Broccoli3, or dBroccoli.

6. The fluorogenic nucleic acid molecule according to of claim 1, wherein the fluorescent molecule-binding regions each consist of a base sequence represented by SEQ ID NO: 16 or 17.

7. The fluorogenic nucleic acid molecule according to claim 1, which contains 4 or more of the fluorescent molecule-binding aptamer sequences.

8. The fluorogenic nucleic acid molecule according to claim 1, wherein fluorescent molecules binding to the fluorescent molecule-binding aptamer sequences are fluorescent molecules of a DFHBI family.

9. A vector comprising:

a promoter that controls expression of a foreign gene;

a restriction enzyme site that is downstream side of the promoter and used for inserting a coding region of the foreign gene; and a 3' untranslated region that is downstream side of the restriction enzyme site, wherein the 3' untranslated region contains a base sequence encoding the fluorogenic nucleic acid molecule according to claim 1.

10. A target RNA fluorescent labeling method that is a method of fluorescently labeling a target RNA, the method comprising:

directly or indirectly linking the fluorogenic nucleic acid molecule according to claim 9 to a target RNA; and then bringing the fluorogenic nucleic acid molecule into contact with fluorescent molecules to which the fluorescent molecule-binding aptamer sequences in the fluorogenic nucleic acid molecule bind.

11. The fluorescent labeling method for a target RNA according to claim 10, wherein the target RNA is a transcript of a target gene, and the fluorescent molecules to which the fluorescent molecule-binding aptamer sequences in the fluorogenic nucleic acid molecule bind are introduced into a cell in which a base sequence encoding the fluorogenic nucleic acid molecule is incorporated into a 3' untranslated region of the target gene, so that the fluorescent molecules bind to the transcript of the target gene.

12. A target RNA fluorescent labeling method that is a method of fluorescently labeling a target RNA, the method comprising:

mixing a sample containing a target RNA with a nucleic acid molecule which is obtained by directly or indirectly linking a probe to be hybridized with a part of the target RNA to the fluorogenic nucleic acid molecule according to claim 1 and fluorescent molecules to which the fluorescent molecule-binding aptamer sequences in the nucleic acid molecule bind.

13. A method of detecting a fluorescence signal emitted from a fluorescent molecule bound to a fluorogenic nucleic acid molecule, the method comprising:

binding a fluorescent molecule of a DFHBI family to the fluorogenic nucleic acid molecule according to claim 8;

then continuously illuminating the fluorogenic nucleic acid molecule for a certain period of time with excitation light for the fluorescent molecule of the DFHBI family; and detecting a value of brightness obtained by subtracting a value of brightness of a fluorescence signal at an illumination end point from a value of brightness of a fluorescence signal at an illumination start point as a fluorescence signal emitted from the fluorescent molecule of the DFHBI family bound to the fluorogenic nucleic acid molecule.

14. The method of detecting a fluorescence signal emitted from a fluorescent molecule bound to a fluorogenic nucleic acid molecule according to claim 13, further comprising:

repeatedly illuminating the fluorogenic nucleic acid molecule bound to the fluorescent molecule of the DFHBI family with the excitation light in multiple illumination cycles each consisting of continuous illumination for a certain period of time followed by interruption of illumination for a certain period of time;

detecting a fluorescence signal at the illumination start point of the continuous illumination and a fluorescence signal at the illumination end point for each illumination cycle;

averaging values of brightness of fluorescence signals at the illumination start point of the continuous illumination detected for all illumination cycles;

averaging values of brightness of fluorescence signals at the illumination end point of the continuous illumination detected for all illumination cycles; and detecting a value of brightness obtained by subtracting the averaged value of brightness of fluorescence signals at the illumination end point from the averaged value of brightness of fluorescence signals at the illumination start point as a fluorescence signal of the fluorescent molecule of the DFHBI family bound to the fluorogenic nucleic acid molecule.

* * * * *